(12) United States Patent
Thng et al.

(10) Patent No.: US 9,662,030 B2
(45) Date of Patent: May 30, 2017

(54) ELECTROCARDIOGRAPHY DEVICE FOR GARMENTS

(71) Applicant: Verily Life Sciences LLC, Mountain View, CA (US)

(72) Inventors: Florence Thng, Mountain View, CA (US); Russell Norman Mirov, Los Altos, CA (US); Sarel Kobus Jooste, Mountain View, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 135 days.

(21) Appl. No.: 14/503,847

(22) Filed: Oct. 1, 2014

(65) Prior Publication Data
US 2016/0095527 A1   Apr. 7, 2016

(51) Int. Cl.
*A61B 5/0408* (2006.01)
*A61B 5/00* (2006.01)
*A61B 5/04* (2006.01)

(52) U.S. Cl.
CPC ........ *A61B 5/04085* (2013.01); *A61B 5/0059* (2013.01); *A61B 5/0408* (2013.01); *A61B 5/04012* (2013.01); *A61B 5/6804* (2013.01); *A61B 5/6805* (2013.01); *A61B 5/6808* (2013.01)

(58) Field of Classification Search
CPC .. A61B 5/04085; A61B 5/6804; A61B 5/6808
USPC ........................................................ 600/388
See application file for complete search history.

(56) References Cited

U.S. PATENT DOCUMENTS

| 3,568,662 | A | * | 3/1971 | Everett | A61B 5/04284 |
| | | | | | 600/384 |
| 4,122,843 | A | * | 10/1978 | Zdrojkowski | A61B 5/6831 |
| | | | | | 600/382 |
| 7,206,630 | B1 | | 4/2007 | Tarler | |
| 7,797,039 | B2 | | 9/2010 | Koivumaa et al. | |
| 8,369,936 | B2 | | 2/2013 | Farringdon et al. | |
| 8,560,044 | B2 | * | 10/2013 | Kurzweil | A61B 5/0408 |
| | | | | | 600/382 |
| 8,594,771 | B2 | * | 11/2013 | Kohls | A61B 5/0404 |
| | | | | | 600/508 |

(Continued)

OTHER PUBLICATIONS

International Search Report and Written Opinion of International Application No. PCT/US2015/051853 dated Dec. 29, 2015 (mailed Dec. 29, 2015).

*Primary Examiner* — Lee S Cohen
(74) *Attorney, Agent, or Firm* — McDonnell Boehnen Hulbert & Berghoff LLP

(57) ABSTRACT

Devices are described herein including mounts configured to removably mount electrodes and other elements of the devices to a garment (e.g., a close-fitting undergarment) of a wearer. The devices include at least two electrodes configured such that the electrodes are maintained in secure electrical contact with skin of the wearer when the device is so mounted. The devices can be mounted to garments at various locations on the torso of the wearer such that an electrocardiographic signal related to the electrical activity of the heart of the wearer can be extracted from voltage fluctuations between the at least two electrodes. Such devices can be used for continuous logging or other applications of the electrocardiographic signals of the wearer. Such logged electrocardiographic signals could be used to determine a medical or health state of the wearer.

22 Claims, 8 Drawing Sheets

(56) References Cited

U.S. PATENT DOCUMENTS

| | | | |
|---|---|---|---|
| 8,663,106 B2 * | 3/2014 | Stivoric | G06F 19/3418 374/164 |
| 2005/0043641 A1 * | 2/2005 | Ueda | A61B 5/02438 600/509 |
| 2005/0148887 A1 * | 7/2005 | Reiter | A61B 5/0002 600/508 |
| 2006/0264767 A1 | 11/2006 | Shennib | |
| 2009/0012408 A1 | 1/2009 | Nagata et al. | |
| 2009/0018409 A1 | 1/2009 | Banet et al. | |
| 2011/0130640 A1 | 6/2011 | Dunagan et al. | |
| 2012/0136231 A1 | 5/2012 | Markel | |
| 2012/0246795 A1 | 10/2012 | Scheffler et al. | |
| 2013/0281815 A1 | 10/2013 | Varadan | |
| 2014/0031663 A1 * | 1/2014 | Gallego | A61B 5/04085 600/386 |
| 2014/0090146 A1 | 4/2014 | Yeomans et al. | |
| 2014/0100432 A1 * | 4/2014 | Golda | A61B 5/04325 600/301 |
| 2015/0094558 A1 * | 4/2015 | Russell | A61B 5/688 600/391 |

* cited by examiner

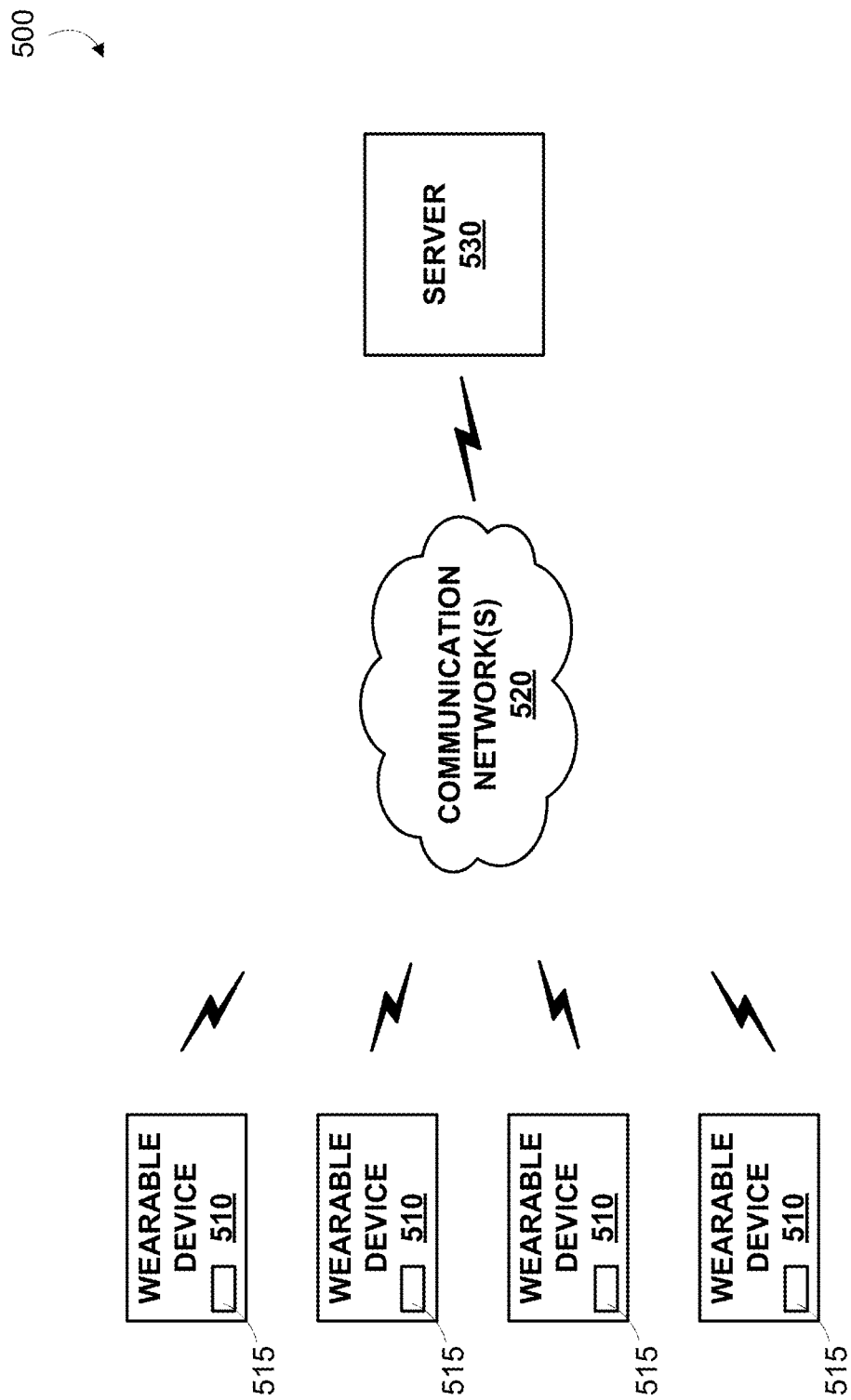

ELECTROCARDIOGRAPHY DEVICE FOR GARMENTS

BACKGROUND

Unless otherwise indicated herein, the materials described in this section are not prior art to the claims in this application and are not admitted to be prior art by inclusion in this section.

Electrocardiography is a technique that records electrical activity of the heart by measuring electrical signals through the skin. The measurements result in a waveform (electrocardiogram) that shows the beating of the heart. The waveform may also include other features that may be indicative of heart health, abnormalities, or medical conditions. The electrocardiographic measurements can be obtained by placing electrodes on the skin at multiple body locations (e.g., on the chest, arms, and/or legs) and electrically connecting the electrodes to a heart monitor. Typically, electrocardiograms are obtained in clinical settings in which a physician, nurse, or other medical professional is involved in placing the electrodes on the body and operating the heart monitor.

SUMMARY

Some embodiments of the present disclosure provide a device including: (i) a reference electrode; (ii) a remote electrode; (iii) a housing; (iv) a signal conditioner disposed in the housing and electrically connected to the reference electrode and the remote electrode, wherein the signal conditioner is configured to extract an electrocardiographic signal from voltage fluctuations between the remote electrode and reference electrode; (v) a first mount configured to removably mount the housing to a garment at a first mounting location; and (vi) a second mount configured to removably mount the remote electrode to the garment at a second mounting location, wherein the second mounting location is separated from the first mounting location.

Some embodiments of the present disclosure provide a device including: (i) a reference electrode; (ii) a remote electrode; (iii) a housing; (iv) means for extracting an electrocardiographic signal from voltage fluctuations between the remote electrode and reference electrode; (v) means for removably mounting the housing to a garment at a first mounting location; and (vi) means for removably mounting the remote electrode to the garment at a second mounting location, wherein the second mounting location is separated from the first mounting location.

Some embodiments of the present disclosure present a method including: (i) removably mounting a device to a garment, wherein the device comprises: (1) a reference electrode; (2) a remote electrode; (3) a housing; (4) a signal conditioner disposed in the housing and electrically connected to the reference electrode and the remote electrode, wherein the signal conditioner is configured to extract an electrocardiographic signal from voltage fluctuations between the remote electrode and reference electrode; (5) a first mount configured to removably mount the housing to the garment at a first mounting location, wherein mounting the device to the garment comprises removably mounting the housing to the garment at the first mounting location; and (6) a second mount configured to removably mount the remote electrode to the garment at a second mounting location, wherein mounting the device to the garment comprises removably mounting the remote electrode to the garment at the second mounting location, wherein the second mounting location is separated from the first mounting location; and (ii) operating the signal conditioner to extract an electrocardiographic signal from voltage fluctuations between the remote electrode and reference electrode.

These as well as other aspects, advantages, and alternatives, will become apparent to those of ordinary skill in the art by reading the following detailed description, with reference where appropriate to the accompanying drawings.

BRIEF DESCRIPTION OF THE DRAWINGS

FIG. 5 is a block diagram of an example system that includes a plurality of devices in communication with a server.

DETAILED DESCRIPTION

Figure 1A:
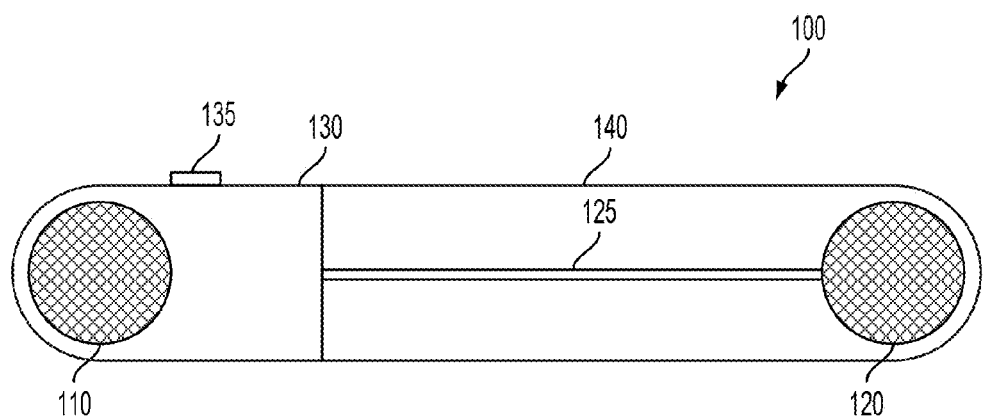
FIG. 1A is a front view of an example device.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

I. OVERVIEW

A device may be configured to measure one or more physiological parameters of a person. The one or more physiological parameters can include an electrocardiographic signal (ECG), which may be related to the electrical activity of the person's heart and, thus, a medical and/or health state of the wearer. To measure an ECG signal, the device may include two electrodes that can be placed in contact with the person's skin at respective locations such as the person's torso, chest, abdomen, pelvis, back, wrist(s), forearm(s), upper arm(s), leg(s), thigh(s), etc. For example, first and second electrodes could contact skin at separate locations on the torso of the person (e.g., at two locations on the chest of the person, on either side of the person's heart), and the ECG signal may be extracted from voltage fluctuations between the first and second electrodes. One or more properties of a detected ECG signal and/or of a plurality of detected ECG signals (detected, e.g., during a plurality of respective periods of time) could be determined and/or related to one or more physiological and/or health states of the person.

Disclosed herein are devices by which a user may obtain electrocardiographic measurements on himself or herself outside of clinical settings. In example embodiments, the device may have a form factor that allows the user to attach the device to a garment (e.g., to an undergarment such as underpants or a brassiere) that is worn by the user (also referred to herein as the wearer). For example, the device may include a housing that houses electronics, a reference electrode mounted on the housing, a remote electrode, and a flexible electrical lead that extends between the housing and the remote electrode. The electronics in the housing may include a signal conditioner, a microprocessor, an analog-to-digital converter (which may be part of the microprocessor), and a wireless transmitter. The signal conditioner may be electrically connected to the reference and remote electrodes and may be configured to extract an electrocardiographic signal from voltage fluctuations between the electrodes. The signal conditioner may, for example, include at least one amplifier, at least one high-pass filter, and at least one low-pass filter (alternatively, one or more of these signal conditioning functions could be performed using software). The microprocessor may obtain data related to the electrocardiographic signal (e.g., after the signal is digitized by the analog-to-digital converter), and the microprocessor may use the wireless transmitter to transmit the data related to the electrocardiographic signal to a remote computing device (e.g., to the "cloud").

The housing may include a mount for removably mounting the housing to the garment at a first mounting location, and the remote electrode may include a mount for removably mounting the remote electrode to the garment at a second mounting location. The mounting locations on the garment could be locations at which the garment presses the reference and remote electrodes against the skin of the wearer (i.e., locations at which the garment exerts significant normal forces into the skin of the wearer). For example, the mounting locations could locations on an elastic waist band of an undergarment. The mounts could be in the form of clips, adhesive strips, pins, flexible hooks, or any other means for removably mounting elements of such a device on or within the garment. When the housing and the remote electrode are properly mounted, the reference electrode contacts the skin at a first location on the user's torso and the remote electrode contacts the skin at a second location on the user's torso. The two torso locations could, for example, be separated by a distance of about 4 to 8 inches. In the case that the device is removably mounted to underpants (e.g., briefs, boxer shorts, panties, etc.), the two torso locations may be locations on the lower abdomen or pelvis. In the case that the device is removably mounted to a brassiere, the two torso locations could be thoracic (chest) locations.

When the device is worn in this way, the wearer may obtain electrocardiographic measurements while involved in certain activities (e.g., while running or engaged in other forms of exercise) or throughout the day. Thus, the device may facilitate continuous or near-continuous cardiac monitoring. Such cardiac monitoring could allow the detection of rare events (e.g., arrhythmias, transient bradycardia and/or tachycardia), cardiac electrical activity during a wider range of wearer behaviors than occur in a hospital or other controlled medical setting, the detection of changes in the electrical activity of the heart over protracted (e.g., weeks, months) periods of time, or other properties of the physiological state of a wearer.

The electronics of the device may include a signal conditioner, a microprocessor, an analog-to-digital converter (which may be part of the microprocessor), data storage, a wireless transmitter, and/or other components. The signal conditioner may be electrically connected to the remote electrode and the reference electrode and may be configured to extract an ECG signal from voltage fluctuations between the electrodes. The signal conditioner may extract the ECG signal by performing various types of signal conditioning, such as amplification, high-pass filtering, and low-pass filtering. Thus, the signal conditioner may include at least one amplifier, at least one high-pass filter, and at least one low-pass filter. Alternatively, one or more of these signal conditioning functions may be formed by software.

The microprocessor may obtain data related to the electrocardiographic signal (e.g., after the signal is digitized by an analog-to-digital converter), and the microprocessor may use the wireless transmitter to transmit the data related to the ECG signal to a remote computing device (e.g., to the "cloud"). Additionally or alternatively, the microprocessor may log the data related to the ECG signal in the data storage. In some examples, the electronics (e.g., the signal conditioner) includes circuitry or other elements configured to detect that the remote electrode and the reference electrode are contacting skin and/or that an ECG signal may be extracted from voltage fluctuations between the electrodes. The device may be operated relative to such a determination; for example, an ECG signal may be extracted using the signal conditioner and logged, transmitted, or used in some other way in response to the determination that the remote electrode and the reference electrode are in contact with skin at respective first and second skin locations (e.g., first and second locations on the torso of the wearer).

The remote electrode and the reference electrode (and any further electrodes) of the device could be configured in a variety of ways to allow the extraction of an ECG signal from voltage fluctuations between the electrodes under a range of physiological and environmental conditions. The electrodes could have a variety of surface compositions to allow ohmic and/or capacitive electrical coupling between the electrodes and skin locations of a wearer. Such surface compositions could include stainless steel, gold, platinum, silver, silver/silver-chloride, polymers or rubbers containing conductive particles, or other conductive or partially conductive materials. Further, the shape and/or surface texture of the electrodes could be specified to allow electrical contact with skin. In some examples, the electrodes could be configured to have a substantially capacitive electrical contact with skin; e.g., the electrodes could include a flat conductor having a substantially nonconductive dielectric coating configured to be in contact with skin. Other compositions and configurations of electrodes are anticipated.

The device could include further sensors. In some examples, this could include the device having additional electrodes configured to provide additional electrophysiological signals (e.g., EMG signals) or other information (e.g., skin resistance, Galvanic skin response). Further sensors could include temperature sensors, light sensors, galvanic sensors, proximity sensors, GPS sensors, accelerometers, or other sensors or combinations of sensors. In some examples, the device could include a photoplethysmographic sensor or some other sensor(s) configured to detect a volume and/or a change in the volume of blood in subsurface vasculature of a wearer. Such detected information could be used, in combination with an extracted ECG signal, to determine one or more properties of the heart and/or vasculature of the wearer. For example, a diastolic, systolic, or other blood pressure of the wearer could be determined.

In some examples, the device may include a wireless communication interface that can transmit data to an external device, for example, using Bluetooth, ZigBee, WiFi, and/or some other wireless communication protocol. The data transmitted by the wireless communication interface may include data indicative of one or more physiological parameters measured by the device, such as extracted ECG signals.

It should be understood that the above embodiments, and other embodiments described herein, are provided for explanatory purposes, and are not intended to be limiting. The terms "garment" and "undergarment" are used herein to refer to any clothing that can be worn by a wearer. In general, some aspect of the garment (e.g., an elastic band) may exert a significant normal force into skin of the wearer. Thus, an electrode (or similar element) adhered, removably mounted, or otherwise disposed on the garment between the skin of a wearer and an aspect of the garment exerting such normal force could be maintained in contact with skin of the wearer by the normal forces exerted by the garment.

Such an aspect of the garment could include a band, cuff, hem, strap, underwire, collar, or sleeve of the garment. Additionally or alternatively, the garment could be wholly or partially form-fitting (e.g., composed wholly or partially of spandex, lycra, or similarly elastic materials or fabrics) and the aspect of the garment could be any form-fitting section of such a garment. Further, an "undergarment" as described herein could be worn beneath some other garment (e.g., under a shirt, pants, a dress). Alternatively, such an undergarment could be worn by a wearer without any other overlaying garments.

Further, "mounting" and/or "removably mounting," as used herein to describe reversibly fixing an element of a device (e.g., a housing, an electrode) to a mounting location of an garment, refer to mounting such elements to such garments such that the element and/or the device can be removed and/or un-mounted from the garment without causing substantial damage and/or change to the garment.

Further, the term "medical condition" as used herein should be understood broadly to include any disease, illness, disorder, injury, condition or impairment—e.g., physiologic, psychological, cardiac, vascular, orthopedic, visual, speech, or hearing—or any situation requiring medical attention.

II. REMOVABLY MOUNTING A DEVICE TO AN GARMENT AND EXTRACTION OF ECG SIGNALS

The heart creates an electric field within the body during the process of pumping blood. The temporal and spatial properties of this field are related to the sum of a plurality of ionic currents that flow within the heart as a result of the depolarization and repolarization of electrically active cells of the heart (e.g., cardiomyocytes) during activity of the heart (e.g., during a heartbeat). This electric field within the body results in voltage fluctuations at the skin (and other locations within the body) being related at least in part to the electrical activity of the heart. As a result, measurement of these voltage fluctuations could be used to detect and/or determine information about the activity of the heart, e.g., to determine a health or medical state (e.g., a disease state) of the heart.

An electrocardiographic (ECG) signal can be extracted from voltage fluctuations between two (or more) location on the skin of a person (e.g., by using electrodes to grant a measurement device electrical access to the two or more skin locations). ECG signals can be extracted from pairs of skin locations on a person, such as between the left and right arms, between the right arm and left leg, between the left arm and left leg, and between pairs of points on the torso (e.g., points on the chest, back, abdomen, pelvis). ECG signals can also be extracted from combinations of voltage fluctuations at more than two skin locations; for example, an ECG signal could be generated based on the difference between the voltage at a first electrode (e.g., an electrode over the heart) and a mean of the voltages of a set of other electrodes (e.g., a mean over the voltages of electrodes at the right arm, left arm, and left leg).

Further, an extracted ECG signal corresponding to a particular heartbeat generally includes a number of temporal features corresponding to phases of the activity of the heart during the particular heartbeat. Specifically, such an extracted ECG signal may include a P wave (corresponding to depolarization of the atria of the heart), QRS complex (corresponding to depolarization of the ventricles of the heart), and a T wave (corresponding to repolarization of the ventricles). Such an extracted ECG signal may include additional features (e.g., a U wave) and/or lack features (e.g., the T wave) according to a medical state of a person, an anatomical or physiological property of the person, and/or the properties of the electrodes and/or measurement equipment used to extract the ECG waveform. One or more properties of the extracted ECG signal (e.g., a Q-T interval, an R-R interval, a P-R interval, an S-T interval, a Q-T interval, an amplitude and/or polarity of a T-wave, and amplitude, polarity, or some other parameter(s) of some other aspect of the ECG signal) could be determined and used to determine a medical and/or health state of the heart and/or of the person containing the heart (e.g., a metabolic rate, a degree of physical exertion, an elevated or depressed level of one or more electrolytes, coronary ischemia, heart attack, cardiac hypertrophy, the presence of certain drugs and/or toxins).

A device could be configured to extract one or more ECG signals from skin of a person by measuring voltage fluctuations between two or more skin locations of the person. This could include accessing the voltage fluctuations at the two or more skin locations by applying respective two or more electrical contacts or electrodes to the two or more skin locations, and electrically connecting the two or more electrical contacts or electrodes to a signal conditioner or other electrical measurement device of the device. This connection could include a flexible lead connecting between a particular skin location and the device, which could be located at some other location on or near the body of the person (e.g., the device could be connected to a belt worn by the wearer, and leads could run from the belt location to electrodes at two skin locations at the wrists of the person). Additionally or alternatively, two or more electrodes could be disposed on the device and configured to contact respective two or more skin locations. The two or more skin locations could be proximate to each other (e.g., the device could be removably mounted on or within a garment worn by the person, and the two or more skin locations could be beneath the garment, such as skin locations beneath the band of underpants and located above either hip of the person). Alternatively, the two or more skin locations could be distant locations and the person could move skin locations of the person's body to contact electrodes of the device.

As an example, a device could be configured to be removably mounted to an undergarment (or other garment worn by a wearer) such that two or more electrodes of the device are maintained in secure electrical contact with skin at respective external body surfaces. This could include removably mounting one or more elements (e.g., a housing, one or more electrodes) of the device beneath a band or other tight-fitting aspect of the garment such that the electrodes contact skin at respective skin locations. The skin locations could be torso locations, thoracic locations, chest locations, back locations, abdominal locations, pelvic locations, arm locations, leg locations, head locations, or any other locations at which voltage fluctuations relating to an ECG signal of the wearer could be detected. A first (e.g., reference) electrode of the device could be disposed on a housing of the device and configured to be in contact with a first skin location when removably mounted to a first mounting location on the garment. The housing could additionally contain electronics or other elements of the device. The device could further include a second (e.g., remote) electrode connected via a flexible electrical lead to the housing (and to electronics therein) and configured to be in contact with a second skin location when removably mounted to a second mounting location on the garment. In this way, the device could enable continuous extraction of ECG signals from voltage fluctuations between the two skin locations (e.g., between skin locations beneath the band of underpants and located above either hip of the person). Such a device could means for performing additional functions, e.g., indicating an alert and/or information about extracted ECG signals to the wearer.

FIG. 1A illustrates such an example device 100. The device 100 includes a reference electrode 110 disposed on a housing 130. The device 100 further includes a remote electrode 120 connected to the housing 130 (and to electronics therein) by a flexible electrical lead 125 (in the example of FIGS. 1A and 1B, the flexible electrical lead 125 takes the form of a conductive trace patterned on a flexible substrate 140 that is connected to the housing 130 and to which the remote electrode 120 is affixed). The device 100 additionally includes electronics (e.g., a signal conditioner, not shown) electrically connected to the reference electrode 110 and the remote electrode 120 (via the flexible electrical lead 125) and configured to extract an ECG signal (related, e.g., to electrical activity of the heart of a wearer) from voltage fluctuations between the reference electrode 110 and the remote electrode 120.

Figure 1B:
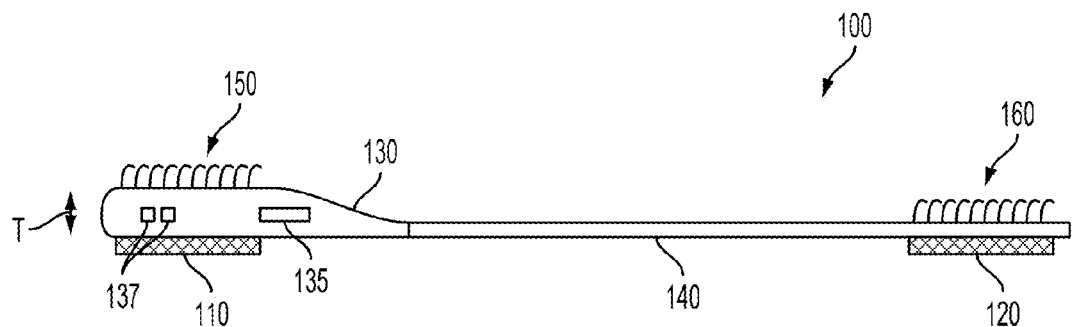
FIG. 1B is a top view of the device illustrated in FIG. 1A.

FIG. 1B illustrates a top view of the device 100. The device 100 further includes a user interface including indicator lights 137 and a button 135 configured for indicating information (e.g., alerts generated based on an extracted ECG signal, alerts received from a system in communication with the device 100, a battery status of a battery of the device 100, an operational status of the device 100) to the wearer and receiving information (e.g., commands) from the wearer, respectively. The housing 130 has a thickness T that is specified to be minimally intrusive (e.g., to minimally interfere with motion of the wearer and/or to minimally discomfort the wearer). In some examples, the thickness T of the housing is between approximately 2.5 millimeters and approximately 3 millimeters. In some examples, the housing comprises a flexible polymer, fabric, or other material configured to protect elements (e.g., electronics) of the device 130 while allowing the device 100 to wholly or partially deform and conform to surfaces of the body of the wearer.

The remote electrode 120 could be connected (electrically and/or mechanically) by a flexible electrical lead 125 in the form of a conductive trace disposed on a flexible substrate 140 that is connected to the housing 130 and to which the remote electrode 120 is affixed, as shown in FIG. 1A. The conductive trace could include copper, tin, or other metals or conductive polymers, conductive liquid crystals, or some other conductive material patterned on the flexible substrate 140. The flexible substrate 140 could be composed of polymers (e.g., Kapton), metal, fiberglass, of some other flexible material. The conductive trace 125 could be deposited, etched, sputtered, drawn and adhered, or otherwise disposed on the flexible substrate 140. Further, elements of the remote electrode 120 could be disposed on the flexible substrate 140 in such a manner, or formed and subsequently adhered to, bonded to, or otherwise disposed on the flexile substrate 140. The remote electrode 120 could additionally or alternatively be electrically and/or mechanically connected to the housing and/or elements therein by some other means.

A first mount 150 and a second mount 160 are included as part of the device 100 and configured to removably mount the housing 130 (and reference electrode 110 disposed thereupon) and remote electrode 120, respectively, to respective first and second mounting locations on or within an garment such that, when a wearer wears the garment with the device 100 mounted thereto, the reference electrode 110 and remote electrode 120 are in contact with respective skin locations of the wearer (e.g., torso locations). As illustrated in FIG. 1B, the mounts 150, 160 each include a plurality of flexible hooks (e.g., using a Velcro® fastener) configured to hook onto fibers of an garment (e.g., to hook onto individual fibers in a fabric panel of an garment). The mounts 150, 160 could include additional or alternative elements configured to mount to aspects of an garment in similar or different ways. In some examples, one or both of the mounts 150, 160 could include a clip configured to clip over an edge of a garment (e.g., over an elastic band at the edge of the garment) or to fabric or other elements of the garment (e.g., a pocket, a flat panel) at a non-edge location. In some examples, one or both of the mounts 150, 160 could include a pin configured to penetrate the garment one or more times to secure elements of the device 100 to the garment (e.g., to penetrate the garment once and then to be capped by a cap or other backing, to penetrate the garment twice and the to be inserted under a protective securing aspect (e.g., a clasp) of the device 100). One or both of the mounts 150, 160 could be configured to mount to an element of garment in some other way.

Figure 2:
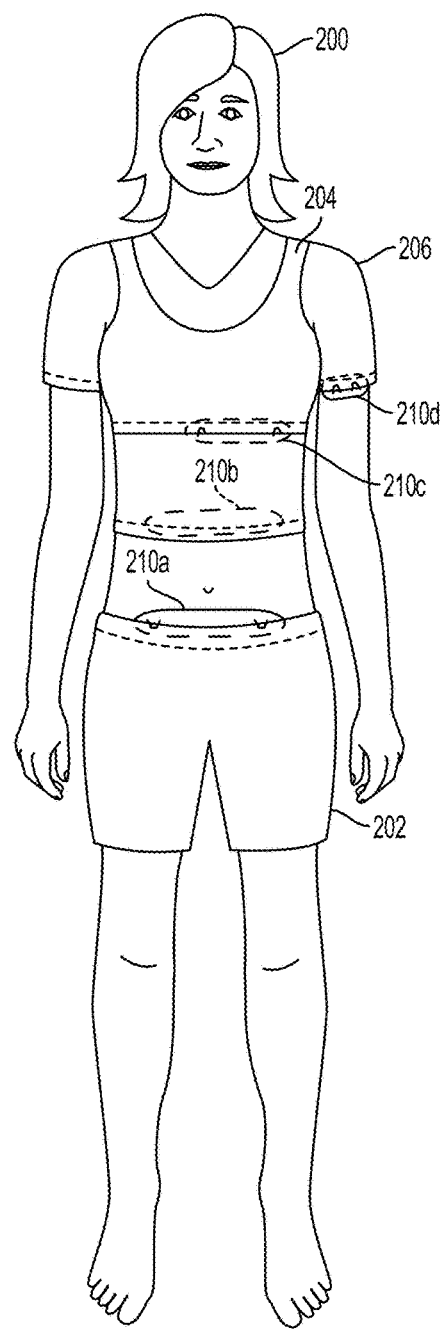
FIG. 2 is a diagram illustrating a number of devices being worn by a person.

FIG. 2 illustrates a wearer 200 who is wearing a variety of garments 202, 204, 206 to which are mounted a variety of devices 210a, 210b, 210c, 210d as described herein. Flexible straps or bands of the garments and elements of devices that are occluded from direct view by overlying elements of garments are illustrated by dashed lines. The garments include shorts 202, a brassiere 204, and a shirt 206 worn over the brassiere 204. A first device 210a is mounted to a band of the shorts 202 such that electrodes of the first device 210a are in contact with skin at pelvic locations on the torso of the wearer 200. A second device 210b is mounted beneath a band of the shirt 206 such that electrodes of the second device 210b are in contact with skin at abdominal locations on the torso of the wearer 200. A third device 210c is mounted to a band of the brassiere 204 such that electrodes of the third device 210c are in contact with skin at thoracic locations on the torso of the wearer 200. A fourth device 210d is mounted to a band of the shirt 206 such that electrodes of the first device 210a are in contact with skin at arm locations on the left arm of the wearer 200.

Properties (e.g., amplitude, polarity, waveform shape, frequency content, presence of various ECG features/waves) of an ECG signal as extracted from electrodes of devices as described herein could be related to the separation distance between, location of, or other properties of the disposition of the electrodes on skin of the wearer and/or the mounting to garments of the wearer. For example, an ECG signal extracted from electrodes disposed at either end of the third device 210c, when positioned at thoracic locations by mounting to the brassiere 204 as shown in FIG. 2, could have a higher amplitude (due, e.g., to proximity to the heart of the wearer) than an ECG signal extracted from electrodes disposed at either end of the first device 210a, when positioned at pelvic locations located above either hip of the wearer 200 by mounting to the shorts 200 as shown in FIG. 2.

Note that the locations, shapes, size, and methods of mounting of the devices 210a, 210b, 210c, 210d and garments 202, 204, 206 illustrated in FIG. 2 are meant as non-limiting examples. Additional mounting locations of devices, methods of mounting devices, undergarments, and other elements of clothing of a wearer are anticipated. It is anticipated that electrodes of a device may be maintained in secure contact with skin at a back, neck, head, arm, torso, leg, pelvic, abdominal, chest, thoracic, gluteal, or other location(s) by mounting to tightly-fitting or otherwise-configured garments.

Mounting locations of electrodes and/or other elements of devices on garments could be any locations of the garments that the devices and/or elements thereof could be mounted to such that one or more electrodes of the devices are maintained in secure electrical contact with skin at respective skin locations of the wearer. Thus, mounting locations could be any tightly-fitting areas of a garment, e.g., a band, cuff, hem, strap, underwire, collar, or sleeve. Additionally or alternatively, the garment could be wholly or partially form-fitting (e.g., composed wholly or partially of spandex, lycra, or similarly elastic materials or fabrics) and the mounting locations could be locations beneath one or more form-fitting sections of such a garment. Further, such mounting locations could be a specified distance apart, at specified locations relative to the garment and/or to anatomical or other landmarks on the wearer's body, or specified in some other way.

For example, mounting locations could be located by a wearer based on an indication from a device, e.g., an indication delivered by the device (e.g., by a light, sound, or other indication generated by an indicator of the device) and/or by some other system in communication with the device (e.g., a visual, textual, acoustical, or other indication generated by a watch, cellphone, or other system in communication with the device). Such an indication could be related to a property of the voltage fluctuations between two or more electrodes of the device, e.g., the device could provide an indication of the strength (or some other metric of signal quality) of ECG signals extracted by the device such that a wearer (or other user) could mount the two or more electrodes at mounting locations that provide ECG signal(s) of sufficient quality for an application.

Note that, as illustrated in FIG. 2, the first 210a, third 210c, and fourth 210d devices are mounted to respective mounting locations on respective garments by clips. Devices could additionally or alternatively be mounted using flexible hooks, pins, snaps, or some other method or methods as described herein. Further, devices could include additional mounts (e.g., corresponding to additional electrodes, housings, or other additional elements of devices) configured to mount to additional respective mounting locations of a garment.

Note that ECG signals extracted using two or more electrodes of a device as described may be related to electrical properties of the body of the wearer 200, of the electrodes, and to properties of respective interfaces between individual electrodes and respective skin locations. Thus, the extracted ECG signals could be related to a dryness of other state of the skin locations, a type of skin at the skin locations, a degree of force applied between the skin locations and respective electrodes (e.g., to a degree of tightness of fit of a garment), or other considerations. Further, the extracted ECG signals could be related to the composition and configuration of the electrodes (e.g., a composition of a surface of the electrodes, a texture of the surface of the electrodes, a geometry of the electrodes). Correspondingly, one or more properties (e.g., an input impedance, a frequency response, a bandwidth, a sensitivity, a maximum input amplitude) of a signal conditioner or other electronics of the device could be specified and/or controlled relative to expected values of those properties of the body of the wearer 200, of the electrodes, and/or of the interface(s) between the electrode(s) and respective skin location(s) (e.g., to allow the extraction of low-noise, high-amplitude, or otherwise optimized ECG signals).

Electrodes of a device as described herein e.g., 100, 210a, 210b, 210c, 210d) could be configured in a variety of ways to allow the extraction of an ECG signal from voltage fluctuations between the electrodes under a range of physiological and environmental conditions. The electrodes could have a variety of surface compositions to allow ohmic (i.e., related to conduction by ionic and/or redox reaction across the surface of the electrodes) and/or capacitive (i.e., related to the accumulation of opposite charges on opposite sides of a surface of the electrodes) electrical coupling between the electrodes and skin locations of a wearer. Such surface compositions could include stainless steel, gold, platinum, silver, silver/silver-chloride, polymers or rubbers containing conductive particles, or other conductive or partially conductive materials. Further, the shape and/or surface texture of the electrodes could be specified to control one or more properties of the electrical interface of the electrodes with skin. For example, the electrodes could have a specified large area in contact with skin, could protrude from a housing toward the skin (e.g., could have a rounded and/or pointed protruding geometry), could be spring-loaded or otherwise reversibly or irreversibly deformable, could have a surface texture (e.g., to increase an effective surface area between a conductor of the electrodes and fluids on the surface of the skin), or could be configured in some other way.

In some examples, the electrodes could be configured to have a substantially capacitive electrical contact with skin; that is, an electrode could engage in substantially no direct ionic and/or redox conduction across the interface between the electrode and the skin. Conduction of currents between such an electrode and the skin could instead consist substantially of the accumulation of opposite charges on respective opposite sides of a substantially nonconductive barrier between a conductor of the electrode and the skin. For example, an electrode could include a flat conductor having a substantially nonconductive dielectric coating configured to be in contact with skin. Additionally or alternatively, an electrode could have a textured conductive surface coated in a conformal layer of substantially nonconductive material. Other compositions and configurations of electrodes are anticipated.

A signal conditioner or other electronics of a device as described herein e.g., 100, 210a, 210b, 210c, 210d) could include a variety of components configured in a variety of ways to allow one or more ECG signals to be extracted from voltage fluctuations between two or more electrodes of the device when the electrodes are contacting appropriate respective skin locations of a wearer and/or to allow other operations and applications. The electronics could include analog and/or digital electronic components to enable analog and/or digital manipulations of electrical signals related to voltage fluctuations between the electrodes. Generally, the electronics include components configured to amplify and filter voltage fluctuations between the electrodes (e.g., one or more amplifiers, buffers, filters, operational amplifiers, resistors, capacitors, inductors, transistors, rectifiers, or some other linear or nonlinear electronic component or combinations thereof). Thus, the signal conditioner could perform hardware-based signal conditioning. Alternatively, the signal conditioner could perform software-based signal conditioning or a combination of hardware-based and software-based signal conditioning.

The signal conditioner could be configured to extract an ECG signal from a band-passed version of the voltage fluctuations between the electrodes. This could include applying the voltage fluctuations to a band-pass filter having a pass-band between approximately 0.05 Hertz and approximately 150 Hertz. Additionally or alternatively, an electronic signal could be digitally sampled and some digital filtering could be performed (e.g., by a processor of the device) to generate an extracted ECG signal. The electronics could include fast recovery circuitry configured to determine that one or more elements (e.g., amplifiers, filters) of the electronics are saturated and to responsively control one or more properties of the electronics (e.g., operate an electronic switch to discharge a capacitor, change a corner frequency or other parameter of a filter) to reduce the electronic saturation of the one or more elements of the electronics. One or more elements of the electronics could become saturated due to an electrostatic discharge (e.g., an electrostatic discharge through a wearer and/or through the device), a voltage fluctuation between the electrodes having a large amplitude, motion of the electrodes relative to skin (e.g., motion of the electrodes relative to the skin could cause a triboelectric voltage fluctuation, an electrostatic voltage fluctuation, or an electrochemical voltage fluctuation), or some other electrical event causing saturation of the one or more elements of the electronics. Other configurations and applications of electronics of the device are anticipated.

A device as described herein e.g., 100, 210a, 210b, 210c, 210d) could include additional sensors. For example, the device could include accelerometers, optical pulse sensors, photoplethysmographic sensors, pulse oximeters, temperature sensors, acoustical sensors, force sensors, electric field sensors, magnetic field sensors, or some other sensor(s) configured to detect one or more properties of a wearer and/or of the environment of the device. In some examples, information from different sensors of the device could be combined to determine one or more properties of the wearer (e.g., to determine a health or medical state of the wearer).

For example, a device could be configured to extract an ECG signal from voltage fluctuations between two or more skin locations of a wearer when mounted at two or more mounting locations on or within a garment worn by the wearer. The device could be further configured to detect a volume of blood in a portion of subsurface vasculature of the wearer at a plurality of points in time (e.g., by illuminating the portion of subsurface vasculature and detecting light responsively received from the portion of subsurface vasculature, i.e., via photoplethysmography) to generate a waveform of the volume of blood in the portion of subsurface vasculature over time. Time differences or other comparisons of features of the extracted ECG signal and the determined volume waveform (e.g., a time difference between a maximum of the volume waveform and a corresponding QRS complex of the ECG signal) could be used to determine a flow rate, a pressure wave speed and/or latency, or other information about the blood in the portion of subsurface vasculature and/or information about the heart and vasculature of the wearer. Further, such determined information could be used to determine a health or medical state of the wearer, e.g., to determine a blood pressure of the wearer, to determine a degree of atherosclerosis of the vasculature of the wearer, etc.

III. EXAMPLE DEVICES

Devices as described herein could be configured in a variety of ways. In some examples, a device could be configured to be mounted by one or more mounts to one or more mounting locations on or within a garment worn by a wearer such that electrodes or other elements of the device are maintained in contact with skin at one or more locations on the body of the wearer. Further, such a device could include a reference electrode disposed on a housing (e.g., on an inside surface of the housing) of the device and configured to contact skin at a first location when the device is mounted to a first mounting location of the garment worn by the wearer. Such a device could additionally include a remote electrode (e.g., connected electrically and/or mechanically to the housing via a tether, cable, or other means) to contact skin at a second location when the remote electrode is mounted to a second mounting location of the garment worn by the wearer such that electronics (e.g., a signal conditioner) of the device could extract an ECG signal from voltage fluctuations between the reference electrode and the remote electrode. Such a device could include additional electrodes configured to be mounted to respective additional mounting locations of the garment, or to mounting locations of some other garment worn by the wearer.

Figure 3A:
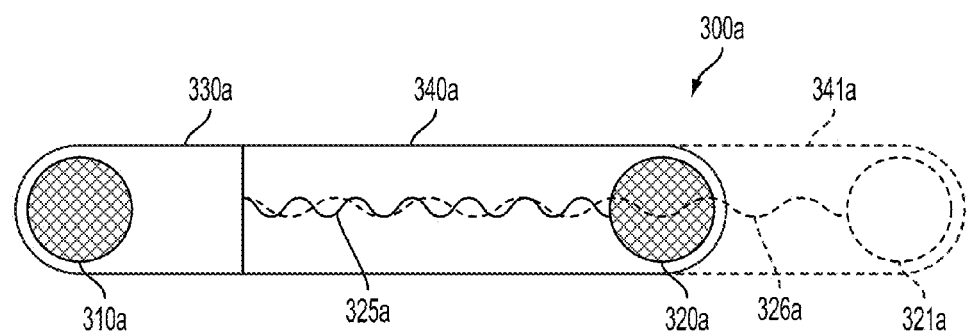
FIG. 3A is a front view of an example device.

As an example, FIG. 3A illustrates a device 300a similar to the devices 100, 210a, 210b, 210c, 210d illustrated in FIGS. 1A and 1B and FIG. 2. The device 300a can be configured to extract an ECG signal from voltage fluctuations between skin at first and second external body surfaces of a wearer accessed via a reference electrode 310a and a remote electrode 320a/321a when mounted on or within a garment worn by the wearer. A separation distance between the first and second external body surfaces can be adjusted by adjusting elements of the device 300a; the configuration of elements of the device 300a (e.g., 320a, 325a, 340a) during a first period of time an having a first separation distance is shown in solid lines, while the configuration of those elements (e.g., 321a, 326a, 341a) during a second period of time and having a second, greater separation distance is illustrated in dashed lines.

The reference electrode 310a is disposed on a housing 330a. Further, the device 300a includes a first mount (not shown) configured to removably mount the housing 330a to a first mounting location (e.g., a band, a strap, a hem, an edge) of the garment. The remote electrode 320a/321a is disposed on an extensible, flexible substrate 340a/341a and includes a second mount (not shown) configured to removably mount the remote electrode 320a/321a to a second mounting location of the garment. The remote electrode 320a/321a is connected to the housing 330a and/or electronics therein (not shown) by a flexible, extensible electrical lead 325a/326a disposed on the flexible substrate 340a/341a. Operated and/or mounted in this way, the reference electrode 310a and remote electrode 320a, 321a could contact skin at the first and second external surfaces of the body, respectively, such that an ECG signal (as measured between the first and second external body surfaces, e.g., between locations above opposite hips of the wearer and separated by a distance of between approximately 4 inches and approximately 8 inches) could be extracted from voltage fluctuations between the reference electrode 310a and remote electrode 320a, 321a.

One or more mounts, such as clips, pins, flexible hooks, snaps, etc. can be provided to mount one or more elements of the device to respective mounting locations of a garment such that the one or more elements of the device are maintained in contact with respective external body surfaces. The mount(s), in combination with the garment (e.g., a tightly-fitting band, strap, hem, or other aspect of the garment), may prevent the one or more elements of the device from moving relative to the body to ensure consistent contact between an electrode or other sensor of the device 300a and the skin to enable consistent extraction of an ECG signal and/or measurement of some other property of the wearer.

The reference electrode 310a and remote electrode 320a, 321a could be composed of an electrically conductive material, such as a metal or a combination of metals, or a nonmetal conductor. The reference electrode 310a and remote electrode 320a, 321a could be composed of the same material or different materials. The reference electrode 310a and remote electrode 320a, 321a could each be composed of a single material or could be composed of multiple materials. For example, the electrodes could have a bulk composed of a first material and a surface plating of another material. For example, the electrodes could have a bulk composed of copper and a surface composed of gold or of gold alloyed with nickel and/or cobalt. Alternatively, the surface layer could be composed of stainless steel, gold, platinum, silver, silver/silver-chloride, polymers or rubbers containing conductive particles, or other conductive or partially conductive materials. The surface layer could be deposited by a number of methods familiar to one skilled in the art; for example, electroplating. Other compositions are possible, as well. Additionally or alternatively, the electrodes could be configured to be substantially capacitively coupled to respective external body surfaces by, e.g., including a flat conductor having a substantially nonconductive dielectric coating configured to be in contact with skin. Other compositions and configurations of electrodes are anticipated. Further, protruding aspects of the electrodes could have an inscribed, cast, and/or pressed texture or pattern. Additionally or alternatively, the exposed aspects of the electrodes could be roughened mechanically, chemically, or by some other method.

One or both of the electrodes could be spring loaded. That is, the electrodes could be configured to include and/or comprise one or more springs or other elements that could be reversibly compressed. An electrode could be spring loaded in a direction perpendicular to an external surface of the body to which the electrode could be mounted. That is, the electrode could be spring loaded in order to improve and/or make more consistent an electrical connection between the electrode and skin of an external body surface to which the electrode is maintained in contact by a garment to which the electrode is mounted.

The housing 330a could be configured to be water-resistant and/or water-proof. That is, the housing could be configured to include sealants, adhesives, gaskets, welds, press-fitted seams, and/or other joints such that the housing 330a is resistant to water entering an internal volume or volumes of the housing 330a when the housing 330a is exposed to water. The housing 330a could further be waterproof, i.e., resistant to water entering an internal volume or volumes of the housing 330a when the housing 330a is submerged in water. For example, the housing 330a could be water-proof to a depth of 1 meter, i.e., configured to resist water entering an internal volume or volumes of the housing 330a when the housing 330a is submerged to a depth of 1 meter. Further, the flexible electrical lead 325a/326a between the housing 330a and the remote electrode 320a/321a could be configured such that the flexible electrical lead 325a/326a is water-resistant and/or water-proof; for example, the flexible electrical lead 325a/326a could include a water-proof or water-resistant insulation, passivation layer (e.g., a layer of polyimide deposited on the flexible electrical lead 325a/326a and the flexible substrate 3401/341a), or some other means for water-proofing the flexible electrical lead 325a/326a.

The device 300a includes electronics (not shown in FIG. 3A) electronically coupled to the reference electrode 310a and the remote electrode 320a/321a. The electronics (e.g., electronics configured as a signal conditioner or otherwise as described herein) are configured to extract an ECG signal from voltage fluctuations between the reference electrode 310a and the remote electrode 320a/321a when the reference electrode 310a and the remote electrode 320a/321a are in contact with respective first and second external surfaces of the body.

The device 300a could be operated based an ECG signal extracted as described herein. For example, the device 300a could be configured to determine a health or other state of a wearer based on an extracted ECG signal. Further, the device 300a could be configured to determine whether the device 300a is mounted to a garment worn by a wearer and/or that an ECG signal can be extracted using the reference electrode 310a and the remote electrode 320a/321a based on a value, a change in value, and/or some other property of a current and/or voltage detected through and/or between the reference electrode 310a and the remote electrode 320a/321a (e.g., a current and/or voltage detected while a voltage and/or current is being applied, by electronics of the device 300a, through and/or across the reference electrode 310a and the remote electrode 320a/321a).

The electronics or other elements of the device 300a could be configured to prevent injury of a wearer and/or damage to the device 300a due to operation of the device to extract an ECG signal from voltage fluctuations between two or more external body surfaces using the reference electrode 310a and the remote electrode 320a/321a. Clamping diodes and/or associated blocking resistors could be included in the device 300a and configured to prevent voltages and/or currents above a certain specified maximum from being applied to the electrodes (and thus to the skin of the wearer) and/or to elements of the device 300a. A blocking capacitor (i.e., a capacitor having a high specified value of capacitance) could be electrically disposed between one or more or the electrodes and electronics of the device 300a to prevent the device 300a from injuring the skin of the external body surface(s) and/or causing electrochemical damage to the electrodes (e.g., by preventing the application of direct current to the skin for a protracted period of time, by ensuring that current injected into the skin through the electrodes is essentially charge-balanced). Other operations and configurations of the device 300a to prevent injury of a wearer and/or damage to the device 300a are anticipated.

The reference electrode 310a and the remote electrode 320a/321a, and any additional electrodes (not shown) of the device 300a could additionally be used for other purposes. For example, electronics disposed in the device 300a could be used to sense a skin resistance, a skin capacitance, a body water content, a body fat content, a Galvanic skin potential (GSP), an electromyographic (EMG) signal, and/or some other physiological signal present at and/or through the electrodes. Additionally or alternatively, the electrodes could be used to detect the presence of a charging device or some other electronic system electrically connected to the electrodes. The electronics could then use the electrodes to receive electrical energy from the charging device or other system to recharge a rechargeable battery of the device 300a and/or to power the device 300a. Such a rechargeable battery could additionally or alternatively be recharged wirelessly using electromagnetic energy received by a coil and other wireless charging circuitry disposed in the device 300a.

Figure 3B:
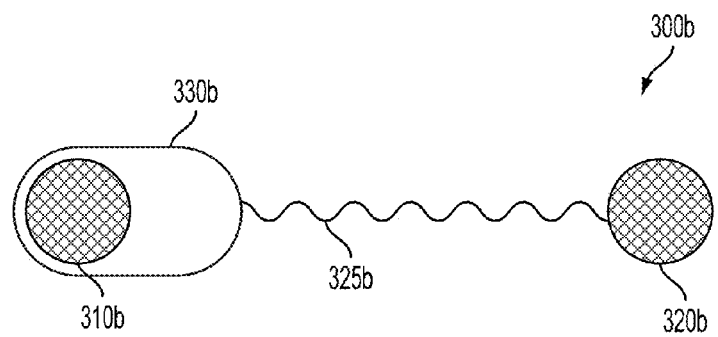
FIG. 3B is a front view of an example device.

As illustrated in FIG. 3A, the device 300a includes a remote electrode 320a/321a disposed on a flexible substrate 340a/341a and mechanically and electrically connected to the housing 330a via the flexible substrate 340a/341a and the flexible electrical lead 325a/326a disposed thereupon. However, a remote electrode of a device as described herein could be electrically and/or mechanically attached to a housing or other element of the device via some other means. For example, FIG. 3B illustrates a device 300b that can be configured to extract an ECG signal from voltage fluctuations between skin at first and second external body surfaces of a wearer accessed via a reference electrode 310b and a remote electrode 320b when mounted on or within a garment worn by the wearer. The reference electrode 310b is disposed on a housing 330b and the remote electrode 320a is connected mechanically and/or electrically to the housing 330b and/or electronics therein by a flexible electrical lead 325b. The flexible electrical lead 325b could include one or more electrical conductors disposed as individual wires or cables and/or braided into multi-strand wires or cables. Individual conductors of the flexible electrical lead 325b could be individually insulated. The flexible electrical lead 325b could additionally include nonconductive elements (e.g., string or rope composed of nylon or some other material, strain reliefs) configured to improve a mechanical property (e.g., a tensile strength) of the flexible electrical lead 325b or according to some other application.

Figure 3C:
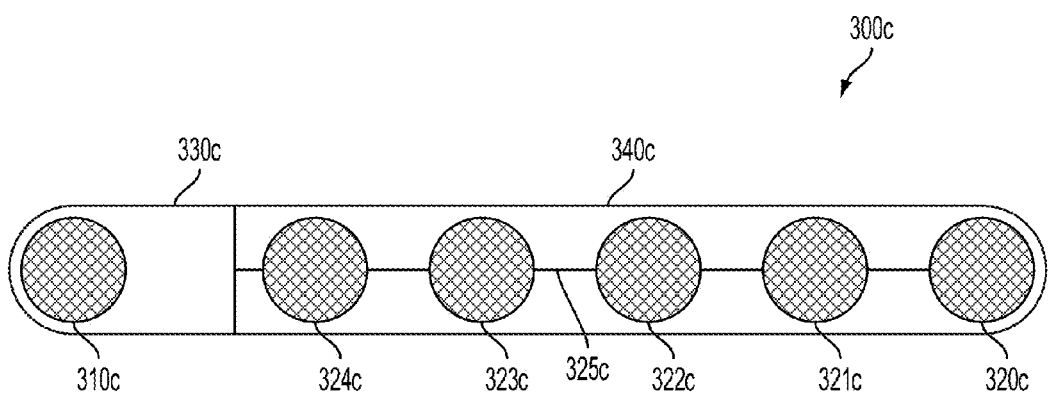
FIG. 3C is a front view of an example device.

Other configurations of a device configured to extract an ECG signal from two or more skin locations of the body when removably mounted on or within garment(s) worn by a wearer are anticipated. Such devices could include more than two electrodes configured to provide additional information to extract additional ECG signals, to extract higher-quality (e.g., higher-magnitude, higher signal-to-noise-ratio) ECG signals, to detect some other information (e.g., to detect a skin resistance, to detect a Galvanic skin response, to detect an EMG signal (e.g., an EMG signal from muscles of the torso of a wearer), or to enable some other application. For example, FIG. 3C illustrates a device 300c that can be configured to extract ECG signals from voltage fluctuations between skin at six separate external body surfaces of a wearer accessed via a reference electrode 310c and remote electrodes 320c, 321c, 322c, 323c, 324c, respectively, when mounted on or within a garment worn by the wearer. The reference electrode 310c is disposed on a housing 330c and the remote electrodes 320c, 321c, 322c, 323c, 324c are disposed on a flexible substrate 340c mechanically connected to the housing 330c. Further, the remote electrodes 320c, 321c, 322c, 323c, 324c are connected electrically to the housing 330c and/or electronics therein by a flexible electrical leads 325c.

The device 300c could include more or fewer electrodes disposed on the housing 330c and flexible substrate 340c than those shown, according to an application. Further, one or more of the remote electrodes 320c, 321c, 322c, 323c, 324c could instead be mechanically and/or electrically connected to the housing 330c and/or electronics thereof by a flexible electrical lead similar to 325b illustrated in FIG. 3B. A plurality of remote and/or reference electrodes of a device could be arranged in a linear array (as illustrated in FIG. 3C) or arranged in some other way according to an application. Further, electronics (e.g., a signal conditioner) of such a device could be configured to generate extracted ECG signals from voltage fluctuations between a signal reference electrode and multiple remote electrodes, between pairs of reference and/or remote electrodes, or according to some other configuration. For example, electronics of a device could generate an ECG signal related to a difference between voltage fluctuations of a first remote electrode and a mean of the voltage fluctuations of a plurality of remote and/or reference electrodes.

Figure 3D:
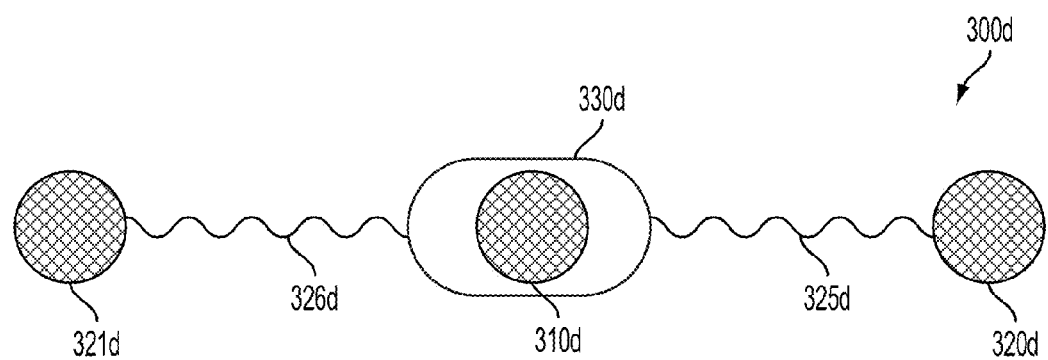
FIG. 3D is a front view of an example device.

In some examples, multiple remote or other electrodes could extend (via flexible electrical leads and/or via flexible substrates) from one or more housings of a device in multiple directions. For example, FIG. 3D illustrates a device 300d that can be configured to extract ECG signals from voltage fluctuations between skin at two external body surfaces of a wearer accessed via a reference electrode 310d and first 320d and second 321d remote electrodes, respectively, when mounted on or within a garment worn by the wearer. The reference electrode 310d is disposed on a housing 330d and the remote electrodes 320d, 321d are connected mechanically and/or electrically to the housing 330d and/or electronics therein by respective flexible electrical leads 325d, 326d.

Figure 3E:
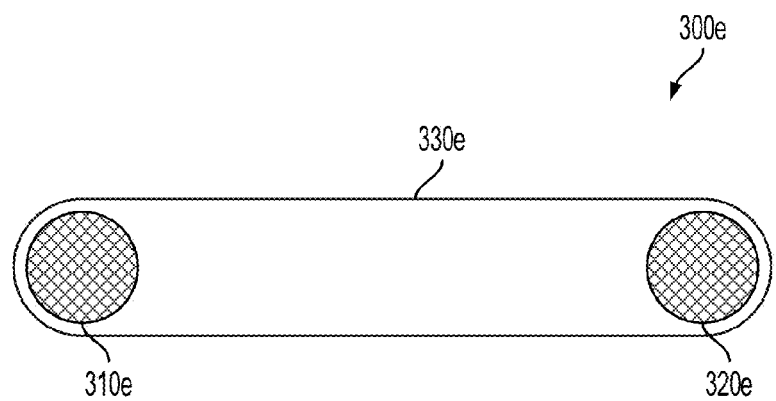
FIG. 3E is a front view of elements of an example device.

In some examples, more than one electrode could be disposed on a housing of a device as described herein. For example, FIG. 3e illustrates a device 300e that can be configured to extract ECG signals from voltage fluctuations between skin at two external body surfaces of a wearer accessed via a reference electrode 310e and a remote electrode 330e when mounted on or within a garment worn by the wearer. The reference electrode 310d and remote electrode 320e are disposed on a housing 330e. In some examples, the housing 330e comprises a flexible polymer, fabric, or other material configured to protect elements (e.g., electronics) of the device 300e while allowing the device 300e to wholly or partially deform and conform to surfaces of the body of the wearer. Additionally or alternatively, elements of the housing could be rigid or otherwise relatively inflexible. In some examples, such rigid or relatively inflexible elements of a housing could be curved or otherwise formed to facilitate mounting on or within a garment and maintained in contact with skin of the wearer by the garment.

In some examples, the device (e.g., a housing 330a, 330b, 330c, 330d, 330e of the device 300a, 300b, 300c, 300d, 300e) further includes at least one detector for detecting at least one other physiological parameter, which could include any parameters that may relate to the health of the person wearing the garment to which the device is removably mounted and/or the environment of the device. For example, the detector could be configured to measure acceleration of the device, a magnetic field, an electric field, an ambient light, a respiration rate, a skin temperature, etc. At least one of the detectors could be configured to non-invasively measure a volume of blood circulating in subsurface vasculature proximate to the device. In a non-exhaustive list, the detector may include any one of an optical (e.g., CMOS, CCD, photodiode), acoustic (e.g., piezoelectric, piezoceramic), electrochemical (voltage, impedance), thermal, mechanical (e.g., pressure, strain, acceleration, rotation), magnetic, or electromagnetic (e.g., RF, magnetic resonance) sensor.

For example, a device could be configured to extract an ECG signal from voltage fluctuations between two or more skin locations of a wearer when removably mounted to a garment worn by the wearer. The device could be further configured to detect a volume of blood in a portion of subsurface vasculature of the wearer at a plurality of points in time (e.g., by illuminating the portion of subsurface vasculature and detecting light responsively received from the portion of subsurface vasculature, i.e., via photoplethysmography) to generate a waveform of the volume of blood in the portion of subsurface vasculature over time (e.g., a photoplethysmographic signal). Time differences or other comparisons of features of the extracted ECG signal and the determined volume waveform (e.g., a time difference between a maximum of the volume waveform and a corresponding QRS complex of the ECG signal) could be used to determine a flow rate, a pressure wave speed and/or latency, or other information about the blood in the portion of subsurface vasculature and/or information about the heart and vasculature of the wearer. Further, such determined information could be used to determine a health or medical state of the wearer, e.g., to determine a blood pressure of the wearer, to determine a degree of atherosclerosis of the vasculature of the wearer, etc.

Devices as described herein could include a variety of mounts and/or mounting means configured and/or operated in a variety of ways to facilitate removably mounting one or more elements (e.g., electrodes, housings) of the devices to respective mounting locations of a garment. Such removable mounting could include substantially non-destructively hooking, clutching, or otherwise attaching to, around, and/or through fibers, fabrics, or other elements of a garment.

Figure 4A:
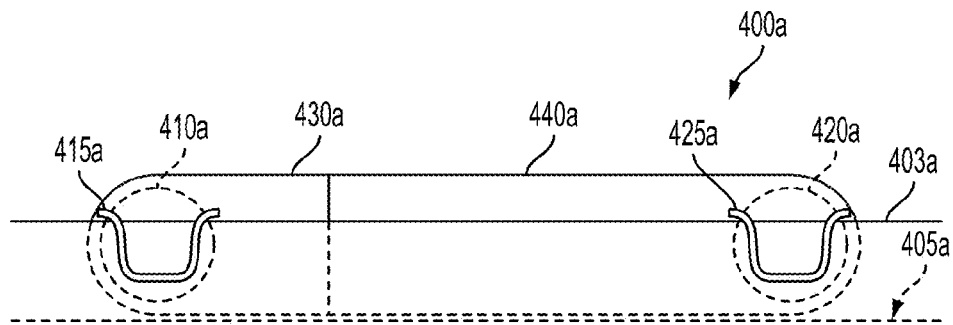
FIG. 4A is a front view of an example device.

As an example, FIG. 4A illustrates a device 400a that can be configured to extract an ECG signal from voltage fluctuations between skin at first and second external body surfaces of a wearer accessed via a reference electrode 410a and a remote electrode 420a (disposed on an opposite side of the device 400a from the view illustrated in FIG. 4A and thus illustrated in dashed lines) when mounted on or within a garment 403a worn by the wearer. The reference electrode 410a is disposed on a housing 430a and the remote electrode 420a is disposed on a flexible substrate 440a connected to the housing 430a. Further, the device 400a includes a first mount 415a (in the form of a clip) configured to clip (i.e., to removably mount) the housing 430a to a first mounting location (e.g., a band, a strap, a hem, an edge) of the garment 403a. The device 400a also includes a second mount 425a (in the form of a clip) configured to clip (i.e., to removably mount) the remote electrode 420a to a second mounting location of the garment 403a. A illustrated in FIG. 4A, the mounts 415a, 425a are mounting the housing 430a and remote electrode 420a, respectively, to mounting locations on a band 405a of the garment 403a disposed along an edge of the garment 403a. The mounts 415a, 425a, in combination with the garment 403a (e.g., a tightly-fitting band of the garment 403a), may prevent the reference electrode 410a and the remote electrode 420a from moving relative to the body to ensure consistent contact between the electrodes 310a, 320a and the skin to enable consistent extraction of an ECG signal and/or measurement of some other property of the wearer. Clip mounts (e.g., 415a, 425a) could be configured and/or operated to mount the housing 430a and remote electrode 420a to other aspects and/or elements of the garment 403a (not shown) according to an application.

Figure 4B:
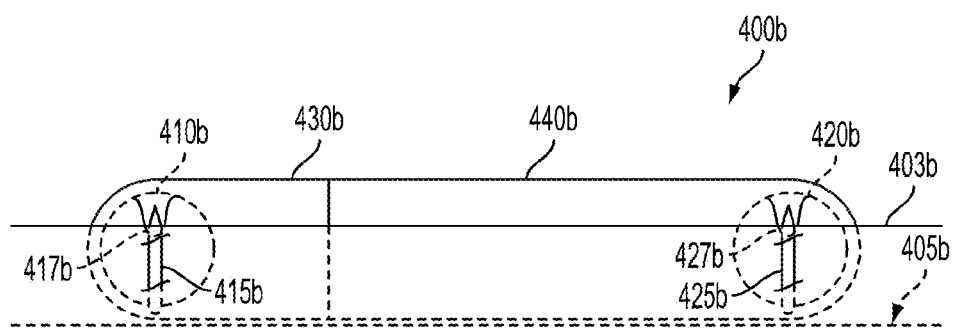
FIG. 4B is a front view of an example device.

Alternatively, one or more mounts of a device as described herein could be configured to substantially non-destructively penetrate an garment one or more times to secure elements of the device to the garment. As an example, FIG. 4B illustrates a device 400b that can be configured to extract an ECG signal from voltage fluctuations between skin at first and second external body surfaces of a wearer accessed via a reference electrode 410b and a remote electrode 420b (disposed on an opposite side of the device 400b from the view illustrated in FIG. 4B and thus illustrated in dashed lines) when mounted on or within a garment 403b worn by the wearer. The device 400b includes a first mount (in the form of a pin 415b and clasp 417b) configured to pin (i.e., to removably mount) the housing 430b to a first mounting location (e.g., a band, a strap, a hem, an edge) of the garment 403b. The device 400b also includes a second mount (in the form of a pin 425b and clasp 427b) configured to pin (i.e., to removably mount) the remote electrode 420b to a second mounting location of the garment 403b. A illustrated in FIG. 4B, the mounts are mounting the housing 430b and remote electrode 420b to mounting locations on a band 405b of the garment 403b disposed along an edge of the garment 403b. The mounts in combination with the garment 403b (e.g., a tightly-fitting band of the garment 403b), may prevent the reference electrode 410b and the remote electrode 420b from moving relative to the body to ensure consistent contact between the electrodes 310b, 320b and the skin to enable consistent extraction of an ECG signal and/or measurement of some other property of the wearer. Pin mounts (e.g., 415b, 417b, 425b, 427b) could be configured and/or operated to mount the housing 430b and remote electrode 420b to other aspects and/or elements of the garment 403b (not shown) according to an application.

Figure 4C:
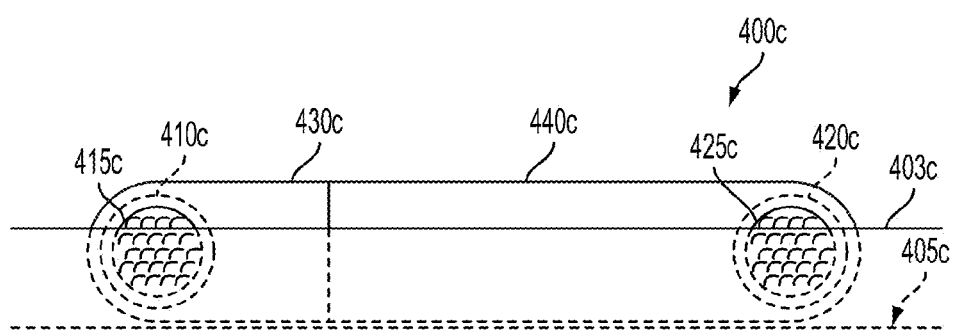
FIG. 4C is a front view of an example device.

In another example, one or more mounts of a device as described herein could be configured to hook onto fibers of a garment using a plurality of flexible hooks (e.g., Velcro) to secure elements of the device to the garment. As an example, FIG. 4C illustrates a device 400c that can be configured to extract an ECG signal from voltage fluctuations between skin at first and second external body surfaces of a wearer accessed via a reference electrode 410c and a remote electrode 420c (disposed on an opposite side of the device 400c from the view illustrated in FIG. 4C and thus illustrated in dashed lines) when mounted on or within a garment 403c worn by the wearer. The device 400c includes a first mount 415c (in the form of a plurality of flexible hooks configured to hook onto fibers of a fabric or other element(s) of the garment 403c) configured to removably mount the housing 430c to a first mounting location (e.g., a band, a strap, a hem, an edge) of the garment 403c. The device 400c also includes a second mount 425c (in the form of a plurality of flexible hooks configured to hook onto fibers of a fabric or other element(s) of the garment 403c) configured to removably mount the remote electrode 420c to a second mounting location of the garment 403c. A illustrated in FIG. 4C, the mounts 415c, 425c are mounting the housing 430c and remote electrode 420c to mounting locations on a band 405c of the garment 403c disposed along an edge of the garment 403c. The mounts 415c, 425c in combination with the garment 403c (e.g., a tightly-fitting band of the garment 403c), may prevent the reference electrode 410c and the remote electrode 420c from moving relative to the body to ensure consistent contact between the electrodes 310c, 320c and the skin to enable consistent extraction of an ECG signal and/or measurement of some other property of the wearer. Flexible hook mounts 415c, 425c could be configured and/or operated to mount the housing 430c and remote electrode 420c to other aspects and/or elements of the garment 403c (not shown) according to an application.

Further types, configurations, and operations of mounts configured to removably mount elements (e.g., housings, electrodes) of devices as described herein to garments are anticipated. Such mounts could include dry adhesives, removable (e.g., water-soluble, washable) adhesives, or other elements or substances configured to removably mount to a garment. In some examples, such mounts could include magnetic elements, e.g., first and second magnets and/or high-permeability materials (e.g., soft iron) configured to attract each other through fabric or other elements of a garment. For example, a device could include a permanent magnet disposed in a housing and a soft iron button. A wearer could removably mount the device to an garment by placing the housing on one side of a mounting location of the garment (e.g., one side of fabric of a band of the garment) and disposing the button on the opposite side of the mounting location such that the permanent magnet exerts an attractive magnetic force on the button sufficient to prevent movement of the housing relative to the mounting location. In some examples, removably mounting a device on or within a garment could include placing the device in a pocket of the garment, snapping a snap of the device to a corresponding snap included in the garment, or using some other aspect of the garment that is configured to facilitate mounting such a device to the garment. Other methods for removably mounting a device as described herein on or within a garment worn by a wearer to facilitate extraction of an ECG signal related to the wearer are anticipated.

FIG. 5 is a simplified schematic of a system 500 including one or more devices 510. The one or more devices 510 may be configured to transmit data via a communication interface 515 over one or more communication networks 520 to a remote server 530. In one embodiment, the communication interface 515 includes a wireless transceiver for sending and receiving communications (e.g., indications of a measured skin resistance and/or capacitance) to and from the server 530. In further embodiments, the communication interface 515 may include any means for the transfer of data, including both wired and wireless communications. For example, the communication interface 515 may include a universal serial bus (USB) interface or a secure digital (SD) card interface. Communication networks 520 may include any of: a plain old telephone service (POTS) network, a cellular network, a fiber network and a data network. The server 530 may include any type of remote computing device or remote cloud computing network. Further, communication network 520 may include one or more intermediaries, including, for example wherein the device 510 transmits data to a mobile phone or other personal computing device, which in turn transmits the data to the server 530.

In addition to receiving communications from the device 510, such as data regarding health and/or affect state as input by the user or extracted electrocardiographic (ECG) signals or other sensor data, the server may also be configured to gather and/or receive either from the device 510 or from some other source, information regarding a wearer's overall medical history, environmental factors and geographical data. For example, a user account may be established on the server for every wearer that contains the wearer's medical history. Moreover, in some examples, the server 530 may be configured to regularly receive information from sources of environmental data, such as viral illness or food poisoning outbreak data from the Centers for Disease Control (CDC) and weather, pollution and allergen data from the National Weather Service. Further, the server may be configured to receive data regarding a wearer's health state from a hospital or physician. Such information may be used in the server's decision-making process, such as recognizing correlations and in generating clinical protocols.

Additionally, the server may be configured to gather and/or receive the date, time of day and geographical location of each wearer of the device during each measurement period. If measuring physiological parameters of the user (e.g., extracted ECG signals), such information may be used to detect and monitor spatial and temporal spreading of diseases. As such, the device may be configured to determine and/or provide an indication of its own location. For example, a device may include a GPS system so that it can include GPS location information (e.g., GPS coordinates) in a communication to the server. As another example, a device may use a technique that involves triangulation (e.g., between base stations in a cellular network) to determine its location. Other location-determination techniques are also possible.

Further, some embodiments of the system may include privacy controls which may be automatically implemented or controlled by the wearer of the device. For example, where a wearer's collected data are uploaded to a cloud computing network for analysis by a clinician, the data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined.

Additionally or alternatively, wearers of a device may be provided with an opportunity to control whether or how the device collects information about the wearer (e.g., information about a user's medical history, social actions or activities, profession, a user's preferences, or a user's current location), or to control how such information may be used. Thus, the wearer may have control over how information is collected about him or her and used by a clinician or physician or other user of the data. For example, a wearer may elect that data, such as health state and physiological parameters, collected from his or her device may only be used for generating an individual baseline and recommendations in response to collection and comparison of his or her own data and may not be used in generating a population baseline or for use in population correlation studies.

IV. EXAMPLE ELECTRONICS DISPOSED IN A DEVICE

Figure 6:
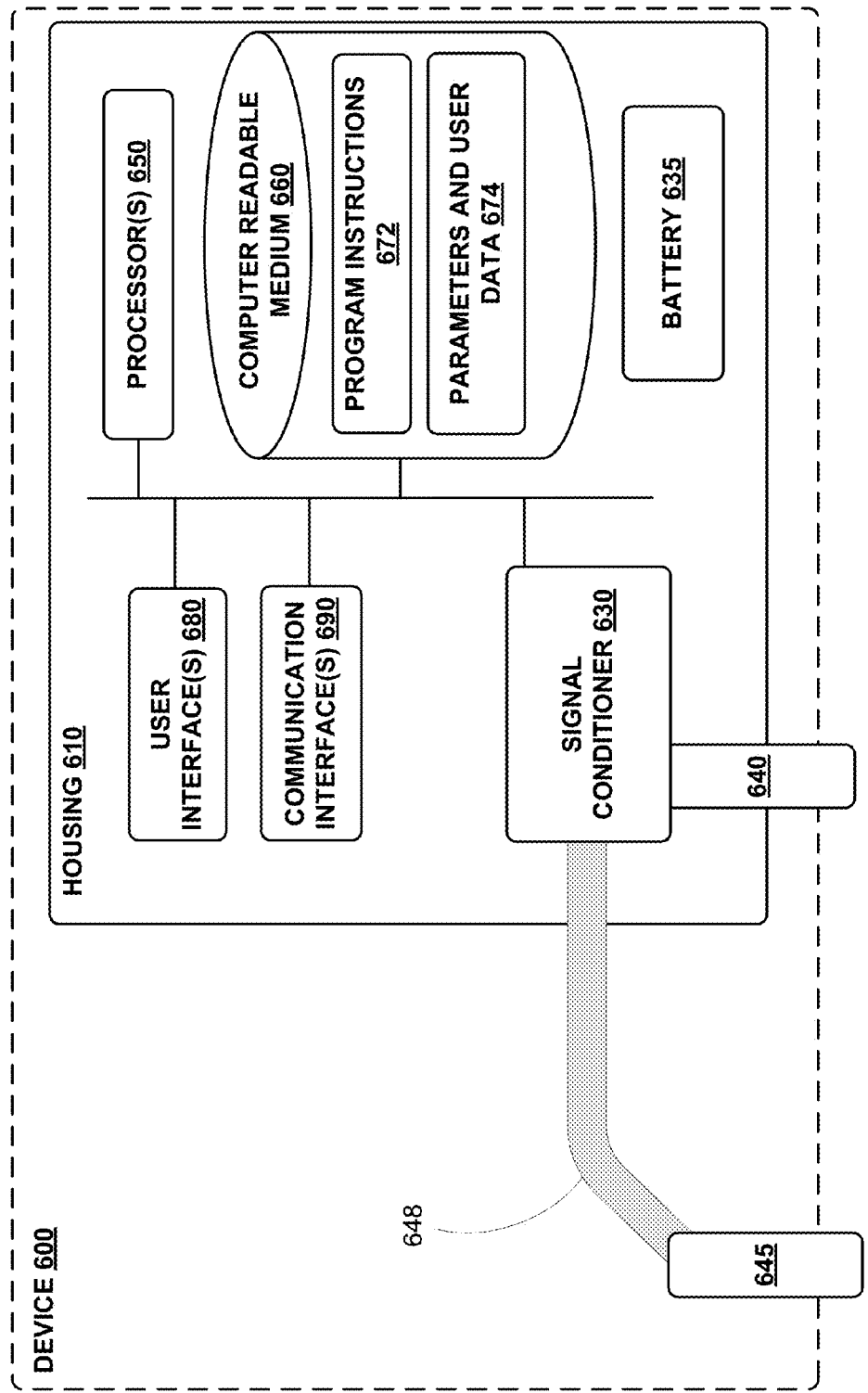
FIG. 6 is a functional block diagram of components disposed in an example device.

FIG. 6 is a simplified block diagram illustrating the components of a device 600, according to an example embodiment. Device 600 may take the form of or be similar to one of device 100, 210a, 210b, 210c, 210d, 300a, 300b, 300c, 300d, 300e, 400a, 400b, and 400c shown in FIGS. 1, 2, 3A-E, and 4A-4C. However, device 600 may also take other forms, for example, a device configured to be mounted within a tightly-fitting garment or undergarment at a leg, neck, back, or other body location.

In particular, FIG. 6 shows an example of a device 600 having a signal conditioner 630 for extracting an electrocardiographic (ECG) signal from voltage fluctuations between two skin locations proximate to reference 640 and remote 645 electrodes of the device 600, a rechargeable battery 635, a user interface 680, communication interface 690 for transmitting data to a server or other remote system, and processor(s) 650. Components (e.g., 630, 635, 640, 650, 680, 690) of the device 600 may be disposed on or within a housing 610. The device 600 further includes a flexible electrical lead 648 configured to electrically connect the remote electrode 645 to the signal conditioner 630. The device 600 could include one or more mounts (not shown) configured to removably mount the electrodes 640, 645 and/or other elements (e.g., the housing 610, elements disposed on or within the housing 610) of the device to an undergarment (or other garment worn by a wearer) such that the electrodes 640, 645 are in electrical contact with respective external body surfaces, e.g., one of the two skin locations from which the signal conditioner 630 is configured to extract an ECG signal.

The signal conditioner 630 uses the reference and remote electrodes 640, 645 to extract an ECG signal from voltage fluctuations between first and second skin locations proximate to respective reference and remote electrodes 640, 645. The signal conditioner 630 could be configured to perform other functions using the reference and remote electrodes 640, 645 and/or further electrodes of the device 600. For example, the signal conditioner 630 could be configured to interface with a charger or other external device or system to power the electronics and to recharge the rechargeable battery 635, to determine that the reference and remote electrodes 640, 645 are in contact with skin and/or that an ECG signal can be extracted from voltage fluctuations between them 640, 645, to determine a skin resistance and/or capacitance between the reference and remote electrodes 640, 645 and/or some other electrodes, or some other function(s). Additionally or alternatively, the rechargeable battery 635 could be charged wirelessly using a coil and/or other components of the device 600 (not shown).

Processor 650 may be a general-purpose processor or a special purpose processor (e.g., digital signal processors, application specific integrated circuits, etc.). The one or more processors 650 can be configured to execute computer-readable program instructions 672 that are stored in a computer readable medium 660 (i.e., data storage) and are executable to provide the functionality of a device 600 described herein.

The computer readable medium 660 may include or take the form of one or more non-transitory, computer-readable data storage media that can be read or accessed by at least one processor 650. The one or more computer-readable storage media can include volatile and/or non-volatile storage components, such as optical, magnetic, organic or other memory or disc storage, which can be integrated in whole or in part with at least one of the one or more processors 650. In some embodiments, the computer readable medium 660 can be implemented using a single physical device (e.g., one optical, magnetic, organic or other memory or disc storage unit), while in other embodiments, the computer readable medium 660 can be implemented using two or more physical devices.

The signal conditioner 630 could include a variety of components configured in a variety of ways to allow one or more ECG signals to be extracted from voltage fluctuations between the reference and remote electrodes 640, 645 when the electrodes 640, 645 are contacting appropriate respective skin locations of a wearer and/or to allow other operations and applications. The signal conditioner 630 could include analog and/or digital electronic components to enable analog and/or digital manipulations of electrical signals related to voltage fluctuations between the electrodes 640, 645. In some examples, the signal conditioner 630 could include one or more analog electronic components (e.g., amplifiers, transistors, op-amps, analog filters) assembled into an analog front-end and configured to amplify, buffer, filter, or otherwise act on voltage fluctuations between the electrodes 640, 645 and to present one or more analog electronic outputs. The signal conditioner 630 may further include an analog-to-digital converter (ADC) to provide a digital output, or signal conditioner 630 may provide an analog output to another component in the device 600 that includes an ADC (e.g., processor 650 may include an ADC).

Generally, the signal conditioner 630 includes components configured to amplify and filter voltage fluctuations between the electrodes 640, 645. The signal conditioner 630 could include one or more amplifiers, buffers, filters, operational amplifiers, resistors, capacitors, inductors, transistors, rectifiers, or some other linear or nonlinear electronic component or combinations thereof. Such components could be formed as a number of discrete signal processing blocks (e.g., discrete sets of components configured to perform some operation(s) on electronic input(s) to form electronic output(s)) that are connected together (e.g., the output(s) of a first block form the input(s) of one or more other blocks).

In some embodiments, the signal conditioner 630 could be configured to extract an ECG signal from a band-passed version of the voltage fluctuations between the electrodes 640, 645. This could include applying the voltage fluctuations to a band-pass filter having a pass-band between approximately 0.05 Hertz and approximately 150 Hertz. The signal conditioner 630 could additionally apply a notch filter (at, e.g., approximately 60 Hertz) to remove some narrow-band signal from the voltage fluctuations (e.g., to remove approximately 60 Hertz noise emitted by power mains in the environment of the device 600). Additionally or alternatively, an electronic signal could be digitally sampled and some signal filtering could be performed (e.g., by the processor 650) to generate an extracted ECG signal. In such examples, the processor 650 and elements thereof (e.g., an ADC of the processor) could be considered part of an overall signal conditioner configured to extract an ECG signal from voltage fluctuations between the electrodes 640, 645.

The signal conditioner 630 could include a fast response circuit or other circuitry or components configured to allow the signal conditioner 630 to extract an ECG signal after the voltage fluctuations between the electrodes 640, 645 exhibit a large change (e.g., a change in baseline voltage level, a spike or other transient related to an electrostatic discharge, a skin location coming into and/or leaving contact with one of the electrodes, and/or a skin location moving relative to one or both of the electrodes 640, 645). For example, the signal conditioner 630 could be configured to determine that one or more elements (e.g., amplifiers, op-amps, signal processing blocks) of the signal conditioner 630 are electronically saturated (i.e., outputting a maximal and/or minimal signal level, or having an internal signal that has a maximal or minimal value) and to responsively control one or more properties of the signal conditioner 630 to reduce the electronic saturation of the one or more elements of the signal conditioner 630.

Determining that one or more elements of the signal conditioner are electronically saturated could include sampling an output or other electronic signal of the signal conditioner 630 using an ADC and making a determination related to one or more digital outputs of the ADC, applying an output or other electronic signal of the signal conditioner 630 to a comparator, Schmitt trigger, or other digital component, or some other determination. Further, controlling one or more properties of the signal conditioner 630 to reduce the electronic saturation of the one or more elements of the signal conditioner 630 could include discharging a capacitor, switching in and/or out one or more signal-processing blocks of the signal conditioner 630, and/or changing a corner frequency, pass-band, or other parameter(s) of a filter (e.g., increasing a corner frequency of a high-pass filter to allow the output of the filter to more quickly decay from a saturation level). These methods of control could be implemented by operating one or more electronic switches, transistors, or other elements.

Additionally or alternatively, fast response or other circuitry of the signal conditioner 630 could prevent electronic saturation of one or more elements of the signal conditioner 630 by having a nonlinear property; for example, a metal-oxide varistor or other electronic elements or combinations thereof having a nonlinear current-voltage characteristic (e.g., having a lower resistance and/or impedance at higher voltages than at lower voltages) could be included in the signal conditioner 630 (e.g., could be connected across a filtering or other capacitor, could be connected between a signal line and a ground plane). Fast response or other circuitry of the signal conditioner 630 configured to prevent electronic saturation of one or more elements of the signal conditioner 630 could exhibit hysteresis. For example, fast response circuitry could include a Schmitt trigger configured to close a capacitor-discharging switch when the voltage across the capacitor exceeds a first specified level and to subsequently open the capacitor-discharging switch when the voltage across the capacitor falls below a second specified level.

The signal conditioner 630 could include circuitry or other elements configured to detect and/or determine whether the reference and remote electrodes 640, 645 are in contact with skin and/or that an ECG signal can be extracted from voltage fluctuations between them 640, 645. The signal conditioner 630 could include circuitry (e.g., voltage dividers, relaxation oscillators, current injectors) configured to actively or passively detect an effective resistance and/or capacitance between reference and remote electrodes 640, 645 that could be used to determine that the reference and remote electrodes 640, 645 are in contact with skin and/or that an ECG signal can be extracted therefrom. Such circuitry could additionally be configured and/or operated to detect other properties of a wearer, e.g., a body water content, a body fat content. Additionally or alternatively, the signal conditioner 630 could include circuitry (e.g., comparators, Schmitt triggers, overvoltage sensors, differentiators, fast response circuitry) configured to detect electrostatic discharges, voltage transients, changes in voltage offsets, or other properties of voltage fluctuations between the reference and remote electrodes 640, 645 that are related to the electrodes 640, 645 coming into and/or leaving contact with skin of a wearer.

A voltage sensor of the signal conditioner 630 (and/or of the processor 650) could include one or more comparators, Schmitt triggers, direct-conversion ADCs, successive-approximation ADCs, sigma-delta ADCs, or some other type(s) of ADC. The voltage sensor could include an amplifier, a filter, a sample-and-hold, and/or some other components. Further, individual elements of the signal conditioner 630 could be embodied as respective discrete components.

Additionally or alternatively, one or more elements of the signal conditioner 630 could be incorporated into one or more integrated circuits (e.g., an integrated circuit that includes elements of the processor 650, the communication interface(s) 690, and/or elements of the device 600. In examples where the signal conditioner 630 is included in a device composed of multiple housings or other subassemblies, the elements of the signal conditioner 630 could all be disposed in a single housing or subassembly or elements of the signal conditioner 630 could be disposed in multiple housings or subassemblies and connected using wires, cables, or other means passing between housings or subassemblies.

In some examples, voltage sources, electronic switches, amplifiers, filters, op-amps, voltage sensors (e.g., ADCs, comparators, Schmitt triggers), and/or other elements of the signal conditioner 630 could be elements of a microprocessor (e.g., of 650) that are electronically coupled to a pin of the microprocessor (e.g., logic gates, capacitors, high-impedance electrical switches (e.g., CMOS FETs), or other microelectronics). For example, a voltage source of the signal conditioner 630 could be an internal voltage supply of the microprocessor, and a voltage source switch of the signal conditioner 630 could be a gate of the microprocessor configured to electrically connect the internal voltage supply and/or an internal ground of the microprocessor to a pin of the microprocessor and to appear as a high impedance element when not connecting the pin to the internal voltage supply and/or the internal ground (e.g., to provide a 'three-state' digital output to the pin). An ADC of the microprocessor could additionally be configured to electrically connect to the pin and to act as a voltage sensor of the signal conditioner 630.

In some examples, the signal conditioner 630 could include circuitry to protect elements of the device 600 (e.g., to protect amplifiers, filters, voltage sensors, or other elements of the signal conditioner 630) from high voltages and/or currents present across and/or through the electrodes 640, 645. For example, the signal conditioner 630 could include clamping diodes, blocking resistors, blocking capacitors, electronic switches, or other elements configured to prevent components of the signal conditioner 630 from being damaged by voltages and/or currents at/through the electrodes 640, 645. These elements of the signal conditioner 630 could be configured to protect the device 600 from electrostatic discharges from the environment of the device 600.

The signal conditioner 630 could include additional components. In some examples, the signal conditioner 630 could include a recharger configured to recharge the rechargeable battery 635 and to be powered through the electrodes 640, 645 and/or some additional electrode(s). In some examples, the device 600 could be configured to be mounted on an external charger. The external charger could be configured to apply a voltage and/or current to the electrodes (e.g., 640, 645) sufficient to power the recharger to recharge the rechargeable battery 635. The signal conditioner 630 could include rectifiers, capacitors, or other elements disposed electrically between the recharger and the electrodes (e.g., 640, 645). The rectifiers or other elements could be configured to reduce electrical interference in ECG signal measurements made using the electrodes 640, 645 when the device 600 is removably mounted to a garment worn by a wearer and not mounted to an external charger. Additionally or alternatively, the device 600 could include a coil and other components configured to receive electromagnetic energy (e.g., from a wireless charger) and to recharge the rechargeable battery 635 using the received electromagnetic energy.

The signal conditioner 630 could include components configured to detect an EMG a skin resistance, a skin capacitance, a body water content, a body fat content, a Galvanic skin response, or some other electrical signal using the electrodes 640, 645 and/or some additional electrode(s). The signal conditioner 630 could include components to operate some other sensors (e.g., accelerometers, optical pulse sensors, photoplethysmographic sensors, pulse oximeters, temperature sensors) configured to detect one or more properties of a wearer of the device 600 and/or of the environment of the device 600.

Note that, while the signal conditioner 630, processor(s) 650, rechargeable battery 635, and other components are sometimes described herein as being disposed on or within a single housing, other configurations are anticipated. In some examples, a device could include multiple housings, and the components of the device 600 could be distributed amongst the multiple housings. For example, a first housing could contain some elements of the signal conditioner 630 (for example, ECG signal extraction electronics, temperature sensing electronics) and the reference electrode 640 could protrude from the first housing. A second housing could include the recharger electronics and the rechargeable battery 635 and elements disposed in the second housing could be electrically connected to elements disposed in the first housing. Other numbers of housings, configurations of housings, and dispositions of components within multiple housings are anticipated.

The program instructions 672 stored on the computer readable medium 660 may include instructions to perform or facilitate some or all of the device functionality described herein. For instance, program instructions 672 could include instructions to operate the signal conditioner 630 to extract an ECG signal from voltage fluctuations between the electrodes 640, 645. The program instructions 672 could additionally include instructions to operate other elements of the signal conditioner 630 (e.g., switches, circuit breakers, FETs) to protect other elements of the device 600 that are electrically coupled to the electrodes 640, 645 (e.g., an amplifier and/or voltage sensor of the signal conditioner 630) from being damaged. The program instructions 672 could include instructions to operate based on parameter and user data 674 stored in the computer readable medium 660 and/or modify the parameters and user data 674. For example, the parameters and user data 674 could include calibration data for the device 600 and/or stored ECG signals (and/or features thereof, e.g., Q-T intervals, QRS complex parameters) extracted using the device 600.

The program instructions 672 stored on the computer readable medium 660 could include instructions for operating the signal conditioner 630 to extract an ECG signal from voltage fluctuations between the electrodes 640, 645. The instructions could include instructions to activate and/or set a value of a current source, a voltage source, a programmable resistor, an ADC, one or more electronic switches, and/or some other component(s) of the signal conditioner 630. The instructions could include instructions to set a gain, bandwidth, corner frequency, notch frequency, or other property of an amplifier and/or filter of the signal conditioner 630. The instructions could include instructions to operate a voltage or current sensor to make one or more measurements relating to the voltage between the electrodes 640, 645. The instructions could include instructions to operate a voltage or current sensor to make a series of measurements during a respective series of regularly spaced periods of time relating to the voltage between the electrodes 640, 645.

The instructions could include instructions to determine whether the reference and remote electrodes 640, 645 are in contact with skin and/or that an ECG signal can be extracted from voltage fluctuations between the electrodes 640, 645 and to responsively extract an ECG signal. This could include analyzing voltage fluctuations between the electrodes 640, 645 to determine whether the voltage fluctuations contain ECG signals. Additionally or alternatively, this could include actively or passively sensing an effective resistance and/or capacitance between the electrodes 640, 645 and further determining that the sensed resistance and/or capacitance corresponds to the electrodes 640, 645 being in contact with skin. In some examples, the instructions could include instructions to extract an ECG signal in response to a user input (e.g., in response to a user depressing a button of the device 600 to indicate that the wearer is experiencing some symptoms, is engaging in some activity (e.g., exercise), is about to engage in an activity, has completed an activity, or that an ECG signal should be extracted for some other user-related purpose).

Other instructions in the program instructions 672 relating to the use of the signal conditioner 630 to extract one or more ECG signals from voltage fluctuations between the electrodes 640, 645 are anticipated. The program instructions 672 could include instructions to extract a plurality of ECG signals during a plurality of periods of time using the signal conditioner 630. The program instructions 672 could include instructions to log or otherwise store data related to the extracted ECG signal(s) in the parameters and user data 874 and/or some other data storage.

The instructions could include instructions to operate the device 600 based on an extracted ECG signal(s) and or information related to extracted ECG signal(s). For example, the instructions could describe how to determine a health or other state of a wearer based on extracted ECG signal(s) (e.g., based on a determined heart rate, a determined pulse timing variability, a determined Q-T interval, determined QRS complex parameters, or some other determined property or feature of one or more extracted ECG signals). The instructions could describe how to determine whether the first and second electrodes 640, 645 are in contact with skin and/or that an ECG signal can be extracted from voltage fluctuations between them 640, 645. The instructions could further describe how to operate the device 600 relative to such a determination. For example, one or more elements (e.g., a voltage or current sensor, an amplifier) of the signal conditioner 630 and/or of the device 600 could be disabled and/or operated in a low-power state when the device 600 determines that the reference and remote electrodes 640, 645 are not in contact with skin and/or that an ECG signal cannot be extracted from voltage fluctuations between them 640, 645. Other operations relative to such a determination are anticipated and could be described by the program instructions 672.

The program instructions 672 stored on the computer readable medium 660 could include instructions for operating components of the device 600 (e.g., the signal conditioner 630) to recharge the rechargeable battery 635 and/or to power the device 600 using the rechargeable battery 635. For example, the instructions could include instructions for operating switches or other electrical components to gate power from the electrodes 640, 645 to the recharger and/or from the recharger to the rechargeable battery 635. Additionally or alternatively, the instructions could include instructions to operate a voltage or current sensor (possibly a sensor of the signal conditioner 630) to detect the presence of an external charger in electrical contact with the electrodes 640, 645 and/or to detect a charge state of the rechargeable battery 635. A recharger and/or rectifier elements of the signal conditioner 630 or of other electronics of the device 600 could be passive, that is, they could be configured to recharge the rechargeable battery 635 and/or power the device 600 without direct operation by the processor(s) 650 or other elements of the device 600 (other than the electrodes 640, 645) when the device 600 is mounted to an external charger or other appropriately configured power source. Additionally or alternatively, a coil and other components of a wireless charger of the device 600 could be configured to receive electromagnetic energy and to charge the rechargeable battery 635 using the received electromagnetic energy.

The program instructions 672 can include instructions for operating the user interface(s) 680. For example, the program instructions 672 could include instructions for displaying data about the device 600 (e.g., by operating one or more indicator LEDs of the device, by operating a vibrator or other tactile stimulator of the device), or for indicating one or more alerts generated by the device 600 and/or received from an external system. Further, program instructions 672 may include instructions to execute certain functions based on inputs accepted by the user interface(s) 680, such as inputs accepted by one or more buttons of the user interface(s) 680.

Communication interface 690 may also be operated by instructions within the program instructions 672, such as instructions for sending and/or receiving information via an antenna, which may be disposed on or in the housing 610. For example, the program instructions 672 could include instructions to operate the communication interface 690 to transmit an extracted ECG signal and/or information related to an extracted ECG signal using the communication interface 690 (e.g., using a wireless transmitter of the communication interface 690). The communication interface 690 can optionally include one or more oscillators, mixers, frequency injectors, etc. to modulate and/or demodulate information on a carrier frequency to be transmitted and/or received by the antenna. In some examples, the device 600 is configured to indicate an output from the processor 650 by modulating an impedance of the antenna in a manner that is perceivable by a remote server or other remote computing device.

In some examples, the communication interface(s) 690 could be operably coupled to the electrodes 640, 645 and could be configured to communicate with an external system by using the electrodes 640, 645. In some examples, this includes sending and/or receiving voltage and/or current signals transmitted through the electrodes 640, 645 when the device 600 is mounted onto an external system such that the electrodes 640, 645 are in electrical contact with components of the external system.

In some examples, extracted ECG signals, temperature measurements, wearer profiles, history of device use, health state information input by device wearers and generated recommendations and clinical protocols may additionally be input to a cloud network and be made available for download by a wearer's physician. Trend and other analyses may also be performed on the collected data, such as physiological parameter data and health state information, in the cloud computing network and be made available for download by physicians or clinicians.

Further, extracted ECG signals and/or health state data from individuals or populations of device wearers may be used by physicians or clinicians in monitoring efficacy of a drug or other treatment. For example, high-density, real-time data may be collected from a population of device wearers who are participating in a clinical study to assess the safety and efficacy of a developmental drug or therapy. Such data may also be used on an individual level to assess a particular wearer's response to a drug or therapy. Based on this data, a physician or clinician may be able to tailor a drug treatment to suit an individual's needs.

In response to a determination by instructions contained in the program instructions 672 that a medical condition is indicated, the device 600 may generate an alert via the user interface 680. The alert may include a visual component, such as a flashing light or other operation of an LED or other visual indicator (e.g., a display), an auditory component (e.g., an alarm sound), a tactile component (e.g., a vibration), and/or an electro-haptic component (e.g., an electro-haptic stimulus delivered using the electrodes 640, 645). The indication may prompt a user to view textual or other information presented on a cellphone or other device in communication with the device 600. Such textual or other information could include one or more recommendations, such as a recommendation that the wearer of the device contact a medical professional, seek immediate medical attention, or administer a medication.

V. ILLUSTRATIVE METHODS FOR OPERATING A DEVICE

Figure 7:
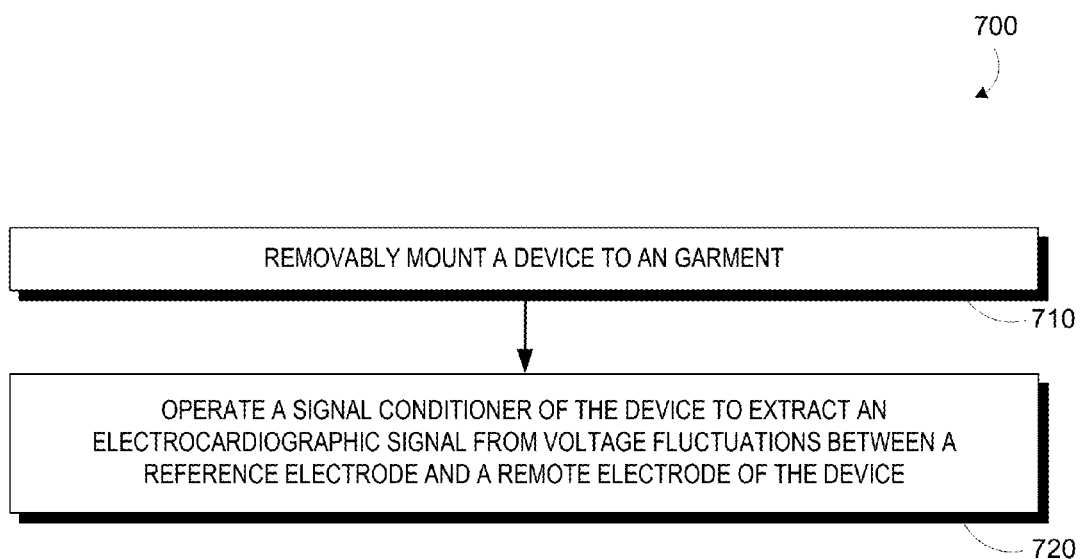
FIG. 7 is a flowchart of an example method.

FIG. 7 is a flowchart of a method 700 for operating a device. The operated device includes (i) a reference electrode, (ii) a remote electrode, (iii) a housing, (iv) a signal conditioner disposed in the housing and electrically connected to the reference electrode and the remote electrode and configured to extract an electrocardiographic (ECG) signal from voltage fluctuations between the reference and remote electrodes, (v) a first mount configured to removably mount the housing to a garment at a first mounting location, and (vi) a second mount configured to mount the remote electrode to the garment at a second mounting location that is separated from the first mounting location.

The method 700 includes removably mounting the device to a garment (710). The garment could be worn by a either before and/or after the device is mounted thereto. Mounting the device could include removably mounting one or more elements (e.g., the housing, the remote and/or reference electrodes) beneath a band or other tight-fitting aspect of the garment (e.g., an elastic band of an undergarment) such that the reference and remote electrodes contact skin at respective first and second skin locations. The skin locations could be torso locations, thoracic locations, chest locations, back locations, abdominal locations, pelvic locations, arm locations, leg locations, head locations, or any other locations at which voltage fluctuations relating to an ECG signal of the wearer could be detected. In some examples, the electrodes or other elements of the device include adhesives and/or conductive gels, and mounting the device to the garment worn by the wearer (710) includes activating, applying, and/or exposing the adhesive and/or conductive material and applying the device to a skin location beneath the garment.

Removably mounting the device to a garment worn by a wearer (710) could include using one or more mounts to removably mount respective elements (e.g., the housing, the remote and/or reference electrodes) of the device to respective mounting locations of the garment. The mounts could include clips configured to clip onto material of the garment, pins configured to penetrate the material of the garment, snaps configured to snap to corresponding elements of the garment and/or to a matching button or other hardware on an opposite side of material of the garment, a plurality of flexible hooks of other means configured to hook onto fibers of the garment (e.g., using a Velcro® fastener), or other means of removably securing elements of the device on or within the garment.

Such mounting locations of the garment could be any locations of the garment that the device and/or elements thereof could be mounted to such that the remote electrode and reference electrode are maintained in secure electrical contact with skin of the wearer. Thus, mounting locations could be any tightly-fitting areas of the garment, e.g., a band, cuff, hem, strap, underwire, collar, or sleeve. Additionally or alternatively, the garment could be wholly or partially form-fitting (e.g., composed wholly or partially of spandex, lycra, or similarly elastic materials or fabrics) and the mounting locations could be locations beneath one or more form-fitting sections of such an garment. Further, such mounting locations could be a specified distance apart, at specified locations relative to the garment and/or to anatomical or other landmarks on the wearer's body, or specified in some other way.

For example, the mounting locations could be located by a wearer based on an indication from the device, e.g., an indication delivered by the device (e.g., by a light, sound, or other indication generated by an indicator of the device) and/or by some other system in communication with the device (e.g., a visual, textual, acoustical, or other indication generated by a watch, cellphone, or other system in communication with the device). Such an indication could be related to a property of the voltage fluctuations between the remote electrode and the reference electrode, e.g., the device could provide an indication of the strength (or some other metric of signal quality) of ECG signals extracted by the device such that a wearer could mount the remote and/or reference electrodes at mounting locations that provide an ECG signal of sufficient quality for an application.

The method 700 also includes operating the signal conditioner of the device to extract an ECG signal from voltage fluctuations between the reference electrode and the remote electrode (720). This could include sampling (e.g., using an ADC or other discrete-time device) a voltage between the reference electrode and the remote electrode a plurality of times during a plurality of respective points in time. This could include amplifying, filtering, level-shifting, inverting, and/or performing some other signal conditioning on the voltage between the reference electrode and the remote electrode using, e.g., one or more amplifiers, filters, op-amps, resistors, inductors, capacitors, other hardware or software element(s), and/or combinations thereof.

The method 700 for operating a device could include additional steps relating to an extracted ECG signal. In some examples, the method 700 could include indicating the extracted ECG signal and/or information related to the ECG signal using a display disposed in the device. In some examples, the method 700 could include wirelessly transmitting the extracted ECG signal and/or information related to the ECG signal using a wireless transmitter disposed in the device. For example, the device could transmit an extracted ECG signal to a remote system (e.g., a server or cloud service accessible to a healthcare provider). In some examples, the method 700 could include logging or otherwise storing the extracted ECG signal and/or information related to the ECG signal using a data storage disposed in the device. In some examples, the method 700 could include operating the device based on the extracted ECG signal and/or information related to the ECG signal. For example, the device could be operated to generate an alert, send a transmission to a remote system, or some other action in response to the extracted ECG signal and/or information related to the ECG signal (e.g., if a Q-T interval of the extracted ECG signal exceeds a threshold).

In another example, the method 700 could include determining whether the reference electrode and the remote electrode are in contact with skin of the wearer. For example, the method could include determining that electrodes are contacting respective skin locations based on a detected capacitance and/or resistance between the electrodes being within a specified range and/or increasing or decreasing at a specified rate. The method could further include operating the device relative to such a determination. For example, extracting an ECG signal using the signal conditioner (720) could be performed in response to the determination that the reference electrode and the remote electrode are in contact with respective first and second external body surfaces. Other applications of a determined resistance and/or capacitance are anticipated.

In some examples, the device could include means for optically detecting the volume of blood in a portion of subsurface vasculature of the wearer at a plurality of points in time, and generating a blood volume waveform over time (i.e., a photoplethysmographic waveform) based on the plurality of detected volumes of blood. Generating such a blood volume waveform could include operating a light source of the device to emit light into the portion of subsurface vasculature through overlying skin and operating a light sensor of the device to receive light responsively reflected, scattered, or otherwise emitted from the portion of subsurface vasculature through the overlying skin. The method 700 could further include using the generated blood volume waveform, in combination with the extracted ECG signal, to determine a blood pressure of the wearer, a degree of atherosclerosis of the vasculature of the wearer, or some other health or medical state of the wearer. This could include determining time differences or other comparisons of features of the extracted ECG signal and the generated blood volume waveform (e.g., a time difference between a maximum of the volume waveform and a corresponding QRS complex of the ECG signal) to determine a flow rate, a pressure wave speed and/or latency, or other information about the blood in the portion of subsurface vasculature and/or information about the heart and vasculature of the wearer.

The example method 700 illustrated in FIG. 7 is meant as an illustrative, non-limiting example. Additional or alternative elements of the method and additional or alternative components of the device are anticipated, as will be obvious to one skilled in the art.

IV. CONCLUSION

Where example embodiments involve information related to a person or a device of a person, the embodiments should be understood to include privacy controls. Such privacy controls include, at least, anonymization of device identifiers, transparency and user controls, including functionality that would enable users to modify or delete information relating to the user's use of a product.

Further, in situations in where embodiments discussed herein collect personal information about users, or may make use of personal information, the users may be provided with an opportunity to control whether programs or features collect user information (e.g., information about a user's medical history, social network, social actions or activities, profession, a user's preferences, or a user's current location), or to control whether and/or how to receive content from the content server that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and used by a content server.

The particular arrangements shown in the Figures should not be viewed as limiting. It should be understood that other embodiments may include more or less of each element shown in a given Figure. Further, some of the illustrated elements may be combined or omitted. Yet further, an exemplary embodiment may include elements that are not illustrated in the Figures.

Additionally, while various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are contemplated herein.

What is claimed is:

1. A device comprising:
   a reference electrode;
   a remote electrode;
   a housing;
   a signal conditioner disposed in the housing and electrically connected to the reference electrode and the remote electrode, wherein the signal conditioner extracts an electrocardiographic signal from voltage fluctuations between the remote electrode and the reference electrode;
   an indicator disposed on or within the housing, wherein the indicator generates a user-discernible indication of signal quality of the extracted electrocardiographic signal;
   a first mount that removably mounts the housing to a garment at a first mounting location; and
   a second mount that removably mounts the remote electrode to the garment at a second mounting location, wherein the second mounting location is separated from the first mounting location.

2. The device of claim 1, wherein at least one of the first mount and the second mount comprises a clip.

3. The device of claim 1, wherein at least one of the first mount and the second mount comprises a pin.

4. The device of claim 1, wherein the reference electrode is disposed on the housing, and wherein the first mount removably mounts the housing to the garment at the first mounting location such that the reference electrode contacts skin at a first torso location.

5. The device of claim 4, wherein the second mount removably mounts the remote electrode to the garment at the second mounting location such that the remote electrode contacts skin at a second torso location, wherein the second torso location is separated from the first torso location.

6. The device of claim 5, wherein the reference electrode and the remote electrode capacitively couple to skin at the first and second torso locations, respectively.

7. The device of claim 1, wherein at least one of the reference electrode and the remote electrode has a surface comprising silver/silver-chloride.

8. The device of claim 1, further comprising a flexible electrical lead extending between the housing and the remote electrode.

9. The device of claim 1, further comprising a wireless transmitter disposed in the housing, wherein the wireless transmitter transmits data related to the electrocardiographic signal.

10. The device of claim 1, further comprising a data storage disposed in the housing, wherein data storage logs data related to the extracted electrocardiographic signal.

11. The device of claim 1, wherein the signal conditioners performs hardware-based and/or software-based signal conditioning, wherein the signal conditioning comprises amplification, high-pass filtering, and low-pass filtering.

12. The device of claim 1, wherein the user-discernible indication comprises light or sound.

13. A method comprising:
   extracting, by a signal conditioner, an electrocardiographic signal from voltage fluctuations between a reference electrode and a remote electrode, wherein the signal conditioner is disposed in a housing and electrically connected to the reference electrode and the remote electrode, wherein the housing is removably mounted to a garment at a first mounting location by a first mount and the reference electrode is removably mounted to the garment at a second mounting location by a second mount, wherein the second mounting location is separated from the first mounting location; and
   generating, by an indicator disposed on or within the housing, a user-discernible indication of signal quality of the extracted electrocardiographic signal.

14. The method of claim 13, further comprising:
   transmitting data related to the extracted electrocardiographic signal using a wireless transmitter disposed in the housing.

15. The device method of claim 13, further comprising:
   logging data related to the extracted electrocardiographic signal using data storage disposed in the housing.

16. The method of claim 13, further comprising determining a health state based on the extracted electrocardiographic signal.

17. The method of claim 13, wherein the garment is an undergarment.

18. The method of claim 13, wherein the user-discernible indication comprises light or sound.

19. The method of claim 13, wherein the reference electrode contacts skin at a first torso location and the remote electrode contacts skin at a second torso location, wherein the second torso location is separated from the first torso location.

20. The method of claim 19, wherein the first and second torso locations are abdominal locations.

21. The method of claim 19, wherein the first and second torso locations are pelvic locations.

22. The device of claim 19, wherein the first and second torso locations are thoracic locations.

* * * * *